(12) United States Patent
Ohashi et al.

(10) Patent No.: US 11,179,748 B2
(45) Date of Patent: Nov. 23, 2021

(54) MOUNTING STRUCTURE, ULTRASONIC DEVICE, ULTRASONIC PROBE, ULTRASONIC APPARATUS, AND ELECTRONIC APPARATUS

(71) Applicant: Seiko Epson Corporation, Tokyo (JP)

(72) Inventors: Koji Ohashi, Matsumoto (JP); Chikara Kojima, Matsumoto (JP); Hiroshi Matsuda, Chino (JP); Hironori Suzuki, Chino (JP); Shuichi Tanaka, Chino (JP)

(73) Assignee: Seiko Epson Corporation

( * ) Notice: Subject to any disclaimer, the term of this patent is extended or adjusted under 35 U.S.C. 154(b) by 844 days.

(21) Appl. No.: 15/973,852

(22) Filed: May 8, 2018

(65) Prior Publication Data

US 2018/0326455 A1 Nov. 15, 2018

(30) Foreign Application Priority Data

May 9, 2017 (JP) .............................. JP2017-092818

(51) Int. Cl.
*B06B 1/06* (2006.01)
*H01L 23/00* (2006.01)
(Continued)

(52) U.S. Cl.
CPC ............... *B06B 1/067* (2013.01); *A61B 8/14* (2013.01); *A61B 8/4427* (2013.01); *A61B 8/4455* (2013.01); *A61B 8/4494* (2013.01); *B06B 1/0629* (2013.01); *G01N 29/245* (2013.01); *H01L 24/13* (2013.01); *H01L 24/16* (2013.01);
(Continued)

(58) Field of Classification Search
CPC combination set(s) only.
See application file for complete search history.

(56) References Cited

U.S. PATENT DOCUMENTS

| 2001/0003656 A1 | 6/2001 | Funaya et al. |
| 2006/0043843 A1 | 3/2006 | Sugiura et al. |
| (Continued) | | |

FOREIGN PATENT DOCUMENTS

| JP | 2001-168265 A | 6/2001 |
| JP | 2006-094459 A | 4/2006 |
| (Continued) | | |

OTHER PUBLICATIONS

Extended European Search Report for Patent Application No. EP18171200.1, dated Sep. 28, 2018 (11 pages).

*Primary Examiner* — Bryan P Gordon
(74) *Attorney, Agent, or Firm* — Harness, Dickey & Pierce, P.L.C.

(57) ABSTRACT

A mounting structure includes a first substrate that has a first surface on which a functional element is provided, a wiring that is provided at a position which is different from a position of the functional element on the first surface, and is connected to the functional element, a second substrate that has a second surface facing the first surface, and a conductor that is provided on the second surface, and is connected to the wiring and the functional element, in which the shortest distance between the functional element and the second substrate is longer than a distance between a position where the wiring is connected to the conductor, and the second substrate.

18 Claims, 29 Drawing Sheets

(51) Int. Cl.
*A61B 8/14* (2006.01)
*A61B 8/00* (2006.01)
*G01N 29/24* (2006.01)
*H01L 41/047* (2006.01)
*H01L 41/053* (2006.01)
*H01L 41/08* (2006.01)
*H01L 41/23* (2013.01)
*H01L 41/29* (2013.01)

(52) U.S. Cl.
CPC .......... *H01L 24/81* (2013.01); *H01L 41/0475* (2013.01); *H01L 41/053* (2013.01); *H01L 41/0825* (2013.01); *H01L 41/23* (2013.01); *H01L 41/29* (2013.01); *B06B 2201/76* (2013.01); *G01N 2291/02466* (2013.01); *G01N 2291/02475* (2013.01); *H01L 2224/13644* (2013.01); *H01L 2224/13655* (2013.01); *H01L 2224/81193* (2013.01); *H01L 2224/81424* (2013.01); *H01L 2224/81439* (2013.01); *H01L 2224/81444* (2013.01); *H01L 2224/81447* (2013.01); *H01L 2224/81455* (2013.01); *H01L 2224/81464* (2013.01); *H01L 2224/81466* (2013.01); *H01L 2224/81471* (2013.01); *H01L 2224/81484* (2013.01); *H01L 2224/81901* (2013.01); *H01L 2924/14* (2013.01)

(56) References Cited

U.S. PATENT DOCUMENTS

| | | |
|---|---|---|
| 2007/0040477 A1 | 2/2007 | Sugiura et al. |
| 2008/0116765 A1 | 5/2008 | Sugiura et al. |
| 2013/0099628 A1* | 4/2013 | Inoue ........................ H03H 3/08 310/313 R |
| 2013/0320803 A1* | 12/2013 | Maeda ................ B81C 1/00293 310/300 |
| 2015/0130326 A1* | 5/2015 | Ishigami ............... H05K 3/4046 310/348 |
| 2017/0028726 A1 | 2/2017 | Sato et al. |
| 2017/0210133 A1* | 7/2017 | Tsukahara ............ B41J 2/14233 |
| 2018/0111372 A1* | 4/2018 | Takabe ................. B41J 2/14233 |

FOREIGN PATENT DOCUMENTS

| | | |
|---|---|---|
| JP | 2007-180166 A | 7/2007 |
| WO | WO-2016-136139 A1 | 9/2016 |
| WO | WO-2017-188125 A1 | 11/2017 |

* cited by examiner

MOUNTING STRUCTURE, ULTRASONIC DEVICE, ULTRASONIC PROBE, ULTRASONIC APPARATUS, AND ELECTRONIC APPARATUS

BACKGROUND

1. Technical Field

The present invention relates to a mounting structure, an ultrasonic device, an ultrasonic probe, an ultrasonic apparatus, and an electronic apparatus.

2. Related Art

When an electronic component is mounted on a circuit substrate, one known mounting method electrically connects a wiring on the circuit substrate side to a wiring on the electronic component side via a bump electrode (for example, refer to JP-A-2007-180166).

JP-A-2007-180166 discloses an electronic component in which an electronic element such as an IC chip and a conductive film as a metal wiring connected to the electronic element are formed on a substrate. An electrode is formed at a peripheral edge portion of the substrate in a part of the conductive film. The circuit substrate is a substrate on which a liquid crystal panel is formed, and an electrode terminal is formed outside a region in which liquid crystal is disposed. The electronic component is bonded to the circuit substrate in a state in which the bump electrodes on the electronic component side are brought into contact with the electrode terminals on the circuit substrate side.

However, in the configuration disclosed in JP-A-2007-180166, the electrode terminal of the circuit substrate is formed outside the region in which a functional element such as liquid crystal is formed, and the bump electrode of the electronic component is formed at the peripheral edge portion of the substrate. The electrode terminal is brought into contact with the bump electrode, and thus a wiring connection between the circuit substrate and the electronic component is performed at a position separated from the functional element.

In the above-described wiring method, in a case where the wiring connection is performed in the region in which the functional element is formed, alignment between the circuit substrate and the electronic component is required to be performed with high accuracy. In other words, in a case where the alignment accuracy is not sufficient, there is concern that the bump electrode may interfere with the functional element. As mentioned above, in the configuration of the related art, it is not easy to perform electrical connection between substrates in the region in which the functional element is formed.

SUMMARY

An advantage of some aspects of the invention is to provide a mounting structure, an ultrasonic device, an ultrasonic probe, an ultrasonic apparatus, and an electronic apparatus, capable of easily performing electrical connection between substrates.

Application Example 1

A mounting structure according to an application example includes a first substrate which has a first surface on which a functional element is provided; a wiring that is provided at a position which is different from a position of the functional element on the first surface, and is connected to the functional element; a second substrate that has a second surface facing the first surface; and a conductor that is provided on the second surface, and is connected to the wiring and the functional element, in which the shortest distance between the functional element and the second substrate is longer than a distance between a position where the wiring is connected to the conductor, and the second substrate.

In this application example, the functional element and the wiring connected to the functional element are provided on the first surface of the first substrate. The conductor connected to the wiring is provided on the second surface of the second substrate. The shortest distance between the functional element and the second substrate is longer than a distance between a position where the wiring is connected to the conductor, and the second substrate. In this configuration, for example, even if a position difference occurs in the conductor when wiring connection is performed around the functional element, it is possible to suppress interference between the conductor and the functional element. Therefore, it is possible to easily perform wiring connection between the first substrate and the second substrate.

Application Example 2

In the mounting structure of the application example, it is preferable that an area of a region in which the conductor is bonded to the second substrate is larger than an area of a region in which the wiring is connected to the conductor.

In this application example, an area of a region in which the conductor is bonded to the second substrate is larger than an area of a region in which the wiring is connected to the conductor. In other words, a sectional area of the conductor in a plane intersecting the first direction is reduced from the second substrate toward the first substrate. In this configuration, a distance between the conductor and the functional element in the plane intersecting the first direction can be increased from the second substrate toward the first substrate on which the functional element is provided. Therefore, it is possible to further suppress interference between the conductor and the functional element. The conductor and the functional element can be disposed to be closer to each other in a plan view viewed from the first direction.

Application Example 3

In the mounting structure of the application example, it is preferable that at least one of the wiring and the conductor includes a resin core and a conductive part covering the resin core.

In this application example, at least one of the wiring and the conductor includes the resin core and the conductive part covering the resin core. In this configuration, when the conductor is brought into contact with the wiring, the resin core can be elastically deformed, and one of the wiring and the conductor can be deformed along the other thereof. Therefore, it is possible to improve close contact between the conductor and the wiring, and thus to improve connection reliability.

Application Example 4

In the mounting structure of the application example, it is preferable that in a first direction directed from the first substrate to the second substrate, a thickness of the resin core at a position overlapping a connection region between the conductor and the wiring is larger than a thickness of the conductive part.

In this application example, a thickness of the resin core is larger than a thickness of the conductive part in the connection region between the conductor and the wiring. The resin core is thicker than the conductive part as mentioned above, and thus the conductor can be easily deformed. Consequently, the stress, when the wiring is brought into contact with the conductor, can be alleviated, and thus it is possible to suppress the occurrence of distortion of the first substrate and the second substrate. Since a thickness of the conductive part is small, and thus the resin core is easily deformed, for example, even if an error occurs in a thickness of the wiring, the wiring can be brought into close contact with the conductor due to deformation of the resin core, and thus it is possible to improve the connection reliability.

Application Example 5

In the mounting structure of the application example, it is preferable that the resin core has a substantially hemispherical shape protruding from the second surface in a case where the conductor is not elastically deformed, and, if the maximum diameter of an end surface of the resin core on the second substrate side is indicated by L, a distance d from the second substrate to the functional element satisfies a relationship of d>L/2.

In this application example, the resin core has a substantially hemispherical shape protruding from the second surface in a state of not being elastically deformed. If the maximum diameter (that is, a diameter) of an end surface of the resin core on the second substrate side is indicated by L, the distance d from the second substrate to the functional element satisfies a relationship of d>L/2. In other words, the distance d is larger than a radius of the resin core before being elastically deformed.

In this configuration, the conductor is elastically deformed, and thus the maximum value of a distance between a tip end thereof and the second substrate is about L/2 (that is, a radius of the resin core). Therefore, the distance d from the second substrate to the functional element is made larger than L/2, and thus it is possible to further suppress interference between the conductor and the functional element.

The conductor may be formed by forming the resin core by heating, melting, and then solidifying a resin, and by coating the resin core with the conductive part.

Application Example 6

In the mounting structure of the application example, it is preferable that the wiring and the conductor intersect each other in a plan view in a first direction directed from the first substrate to the second substrate.

In this application example, the wiring and the conductor intersect each other in the plan view. Consequently, a position difference between the first substrate and the second substrate is allowable in a plane intersecting the first direction during wiring connection, and thus it is possible to prevent the occurrence of defective connection. In other words, in the application example, it is possible to increase an allowable amount for a position difference in the plan view compared with a case where the wiring and the conductor do not intersect each other (for example, a case where the wiring and the conductor are parallel to each other or have point connection). Thus, alignment between the first substrate and the second substrate can be easily performed, and wiring connection can also be easily performed. It is also possible to improve connection reliability.

Application Example 7

In the mounting structure of the application example, it is preferable that at least one of the wiring and the conductor includes a resin core and a conductive part covering at least a part of the resin core.

In this application example, at least one of the wiring and the conductor includes the resin core and the conductive part covering at least a part of the resin core. In this configuration, when the conductor is brought into contact with the wiring, the resin core can be elastically deformed, and one of the wiring and the conductor can be deformed along the other thereof. Therefore, it is possible to improve close contact between the conductor and the wiring, and thus to improve connection reliability.

Application Example 8

In the mounting structure of the application example, it is preferable that one of the wiring and the conductor is longitudinally extended in a second direction which is parallel to the first surface, the other of the wiring and the conductor is longitudinally extended in a third direction which is parallel to the first surface and intersects the second direction, and, in the second direction, a dimension of the conductive part is larger than a dimension of the other of the wiring and the conductor.

In the application example, one of the wiring and the conductor, including the resin core and the conductive part covering the resin core, is longitudinally extended in the second direction, and the other thereof is longitudinally extended in the third direction. In the second direction, a dimension of the conductive part is larger than a dimension of the other of the wiring and the conductor. Consequently, it is possible to maintain connection reliability on the basis of the elastic force while allowing a position difference between the first substrate and the second substrate in the second direction during wiring connection.

Application Example 9

In the mounting structure of the application example, it is preferable that in a case where the wiring is made of a metal material, a ratio of a height of the first surface in a normal direction to a width of the first surface in a surface direction is 0.1 or more and 5 or less.

In this application example, in the wiring, a ratio (aspect ratio) of a height of the first surface in a normal direction to a width of the first surface in a surface direction is 0.1 or more and 5 or less. Consequently, it is possible to prevent the wiring from being deformed when force is applied from the conductor, and thus to improve the reliability of electrical connection.

Application Example 10

In the mounting structure of the application example, it is preferable that the functional element includes a first functional element and a second functional element, and the wiring is connected to the first functional element and the second functional element, and is provided between the first functional element and the second functional element in a plan view in a first direction directed from the first substrate to the second substrate.

In this application example, the functional element is provided on the first surface of the first substrate, and the functional element includes the first functional element and the second functional element. The wiring is connected to the first functional element and the second functional element. The wiring is provided between the first functional element and the second functional element in the plan view in the first direction directed from the first substrate to the second substrate. In other words, a single wiring is connected to the first functional element and the second functional element. Therefore, an area of the wiring can be reduced compared with a case where the wiring for the first functional element only and the wiring for the second functional element only are provided. As a result, the first functional element, the second functional element, and the wiring can be disposed on the first substrate with higher density.

Application Example 11

In the mounting structure of the application example, it is preferable that the functional element includes a vibrator that vibrates along a first direction directed from the first substrate to the second substrate.

In this application example, the functional element is configured to include the vibrator. Also in this configuration, as described above, it is possible to suppress interference between the conductor and the functional element. In other words, it is possible to prevent the conductor from hindering vibration of the vibrator, and thus to appropriately drive the vibrator.

Application Example 12

In the mounting structure of the application example, it is preferable that a connection position between the wiring and the conductor is located further toward the second substrate side than a vibration range of the vibrator in the first direction.

In this application example, a connection position between the wiring and the conductor is located further toward the second substrate side than a vibration range of the vibrator provided on the first substrate. In this configuration, the conductor can be disposed outside the driving range of the vibrator. Consequently, it is possible to further prevent the conductor from hindering vibration of the vibrator, and thus to appropriately drive the vibrator.

Application Example 13

In the mounting structure of the application example, it is preferable that the functional element is an ultrasonic transducer including a flexible film formed on the first substrate, and the vibrator provided on the flexible film.

In this application example, the functional element is an ultrasonic transducer including the flexible film and the vibrator. In this configuration, as described above, it is possible to prevent the conductor from hindering vibration of the vibrator, and thus to appropriately drive the ultrasonic transducer.

Application Example 14

In the mounting structure of the application example, it is preferable that the mounting structure further includes a bond that bonds the first substrate to the second substrate, the first substrate has a functional region in which a plurality of the functional elements are formed, and the bond bonds the first substrate to the second substrate in the functional region.

In this application example, the bond bonds the first substrate to the second substrate in the functional region in which the functional element is formed. Consequently, for example, even in a case where a plurality of conductors and the wirings are provided in the functional region, that is, a plurality of connection positions are present, the uniformity of a distance between the first substrate and the second substrate in the functional region can be improved, and thus the connection reliability at each connection position can be improved.

Application Example 15

An ultrasonic device according to an application example includes a first substrate which has a first surface on which a vibrator is provided; a wiring that is provided at a position which is different from a position of the vibrator on the first surface, and is connected to the vibrator; a second substrate that has a second surface facing the first surface; and a conductor that is provided on the second surface, and is connected to the wiring and the vibrator, in which the shortest distance between the vibrator and the second substrate is longer than a distance between a position where the wiring is connected to the conductor, and the second substrate.

In this application example, the vibrator and the wiring connected to the vibrator are provided on the first surface of the first substrate. The conductor connected to the wiring is provided on the second surface of the second substrate. The shortest distance between the vibrator and the second substrate is longer than a distance between a position where the wiring is connected to the conductor, and the second substrate. In this configuration, in the same manner as in the application example, it is possible to suppress interference between the conductor and the vibrator, to easily perform wiring connection between the first substrate and the second substrate, and also to easily manufacture an ultrasonic device.

Application Example 16

An ultrasonic probe according to an application example includes a first substrate which has a first surface on which a vibrator is provided; a wiring that is provided at a position which is different from a position of the vibrator on the first surface, and is connected to the vibrator; a second substrate that has a second surface facing the first surface; a conductor that is provided on the second surface, and is connected to the wiring and the vibrator; and a case in which the first substrate, the wiring, the second substrate, and the conductor are stored, in which the shortest distance between the vibrator and the second substrate is longer than a distance between a position where the wiring is connected to the conductor, and the second substrate.

In this application example, the vibrator and the wiring connected to the vibrator are provided on the first surface of the first substrate. The conductor connected to the wiring is provided on the second surface of the second substrate. The shortest distance between the vibrator and the second substrate is longer than a distance between a position where the wiring is connected to the conductor, and the second substrate. In this configuration, in the same manner as in the application example, it is possible to suppress interference between the conductor and the vibrator, to easily perform wiring connection between the first substrate and the second substrate, and also to easily manufacture an ultrasonic probe.

Application Example 17

An ultrasonic apparatus according to an application example includes a first substrate which has a first surface on which a vibrator is provided; a wiring that is provided at a position which is different from a position of the vibrator on the first surface, and is connected to the vibrator; a second substrate that has a second surface facing the first surface; a conductor that is provided on the second surface, and is connected to the wiring and the vibrator; and a controller that controls the vibrator, in which the shortest distance between the vibrator and the second substrate is longer than a distance between a position where the wiring is connected to the conductor, and the second substrate.

In this application example, the vibrator and the wiring connected to the vibrator are provided on the first surface of the first substrate. The conductor connected to the wiring is provided on the second surface of the second substrate. The shortest distance between the vibrator and the second substrate is longer than a distance between a position where the wiring is connected to the conductor, and the second substrate. In this configuration, in the same manner as in the application example, it is possible to suppress interference between the conductor and the vibrator, to easily perform wiring connection between the first substrate and the second substrate, and also to easily manufacture an ultrasonic apparatus.

Application Example 18

An electronic apparatus according to an application example includes a first substrate which has a first surface on which a functional element is provided; a wiring that is provided at a position which is different from a position of the functional element on the first surface, and is connected to the functional element; a second substrate that has a second surface facing the first surface; a conductor that is provided on the second surface, and is connected to the wiring and the functional element; and a controller that controls the functional element, in which the shortest distance between the functional element and the second substrate is longer than a distance between a position where the wiring is connected to the conductor, and the second substrate.

In this application example, the functional element and the wiring connected to the functional element are provided on the first surface of the first substrate. The conductor connected to the wiring is provided on the second surface of the second substrate. The shortest distance between the functional element and the second substrate is longer than a distance between a position where the wiring is connected to the conductor, and the second substrate. In this configuration, in the same manner as in the application example, it is possible to suppress interference between the conductor and the functional element, to easily perform wiring connection between the first substrate and the second substrate, and also to easily manufacture an electronic apparatus.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

First Embodiment

Hereinafter, a description will be made of an ultrasonic apparatus according to a first embodiment with reference to the drawings.

Figure 1:
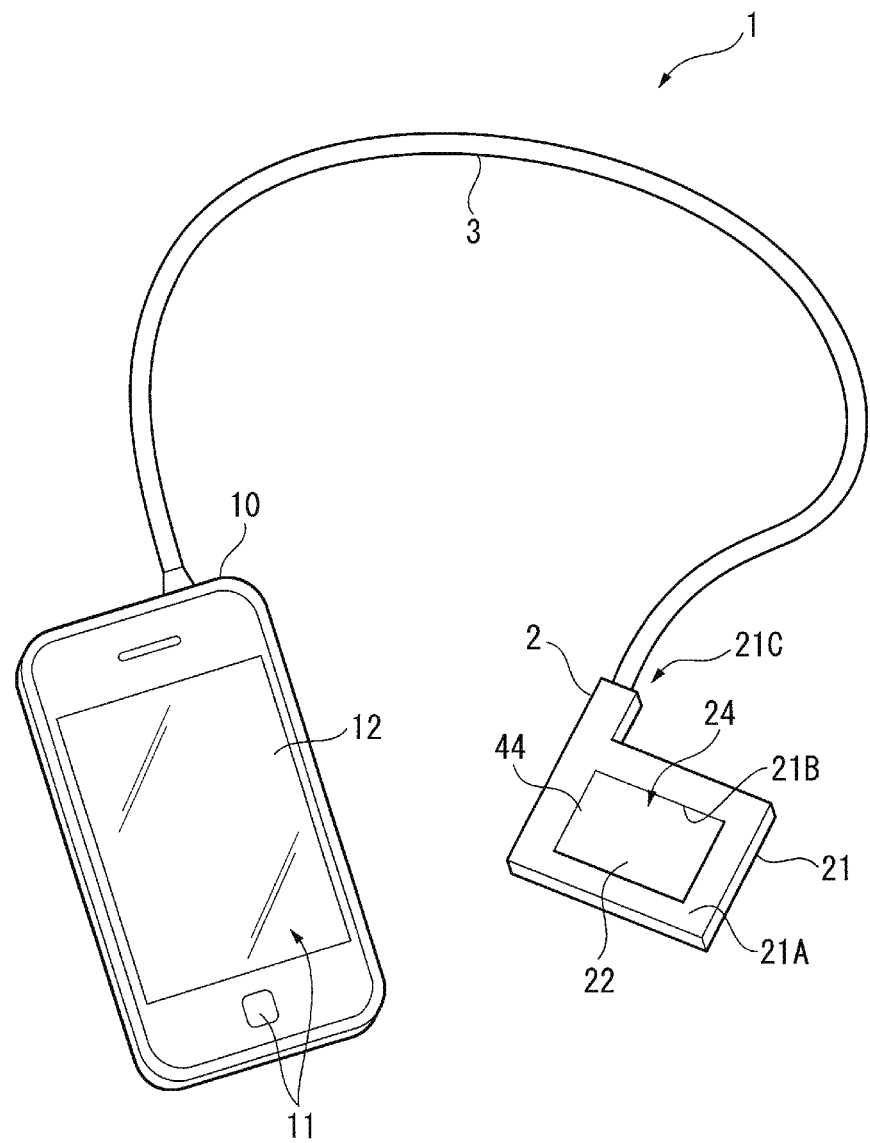
FIG. 1 is a perspective view illustrating a schematic configuration of an ultrasonic apparatus according to a first embodiment.
Figure 2:
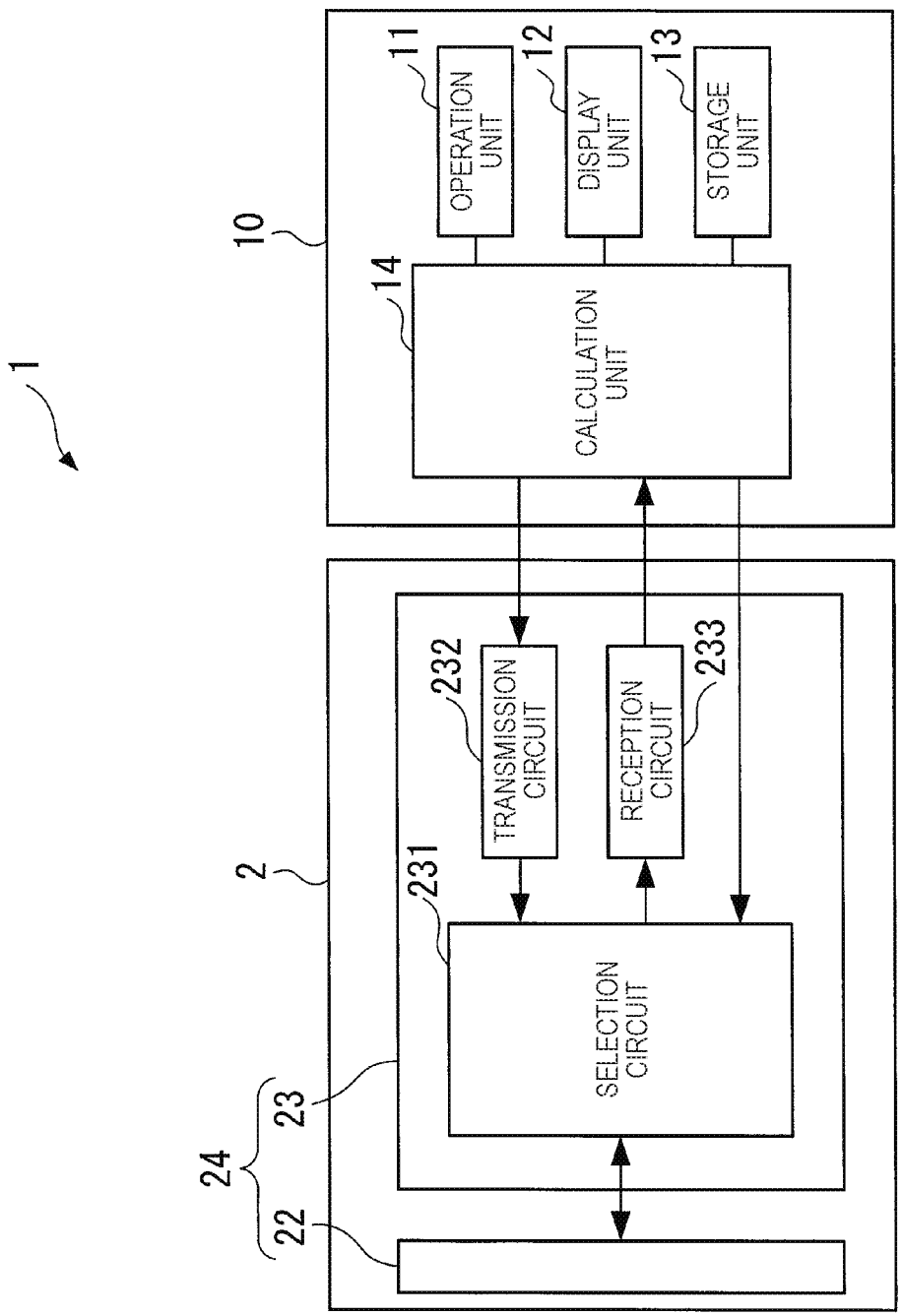
FIG. 2 is a block diagram illustrating a schematic configuration of the ultrasonic apparatus according to the first embodiment.

FIG. 1 is a perspective view illustrating a schematic configuration of an ultrasonic measurement apparatus 1 of the present embodiment. FIG. 2 is a block diagram illustrating a schematic configuration of the ultrasonic measurement apparatus 1.

As illustrated in FIG. 1, the ultrasonic measurement apparatus 1 as an ultrasonic apparatus and an electronic apparatus of the present embodiment includes an ultrasonic probe 2, and a control device 10 as a controller which is electrically connected to the ultrasonic probe 2 via a cable 3.

In the ultrasonic measurement apparatus 1, the ultrasonic probe 2 is brought into close contact with a surface of a living body (for example, a human body), and ultrasonic waves are transmitted into the living body from the ultrasonic probe 2. Ultrasonic waves reflected off an organ of the living body are received by the ultrasonic probe 2, and, for example, an internal tomographic image of the living body is acquired, or a state (for example, a blood flow) of an organ of the living body is measured, on the basis of received signals.

Configuration of Ultrasonic Probe

As illustrated in FIG. 1, the ultrasonic probe 2 includes a case 21, an ultrasonic device 22 stored (housed) in the case 21, and a circuit substrate 23 (refer to FIG. 2) provided with a driver circuit and the like for controlling the ultrasonic device 22. An ultrasonic sensor 24 is formed of the ultrasonic device 22 and the circuit substrate 23, and the ultrasonic sensor 24 forms an ultrasonic module.

Configuration of Case

The case 21 is formed, for example, in a rectangular box shape in a plan view, and a sensor window 21B is provided on one surface (sensor surface 21A) which is orthogonal to a thickness direction, and a part of the ultrasonic device 22 is exposed. A passing hole 21C of the cable 3 is provided at apart of the case 21 (a side surface in the example illustrated in FIG. 1), and the cable 3 is connected to the circuit substrate 23 inside the case 21 through the passing hole 21C. A gap between the cable 3 and the passing hole 21C is filled with, for example, a resin material, and thus water resistance is ensured.

In the present embodiment, a configuration example in which the ultrasonic probe 2 and the control device 10 are connected to each other via the cable 3 is described, but, this is only an example, and, for example, the ultrasonic probe 2 and the control device 10 may be connected to each other through wireless communication, and various constituent elements of the control device 10 may be provided in the ultrasonic probe 2.

Configuration of Ultrasonic Device

Figure 3:
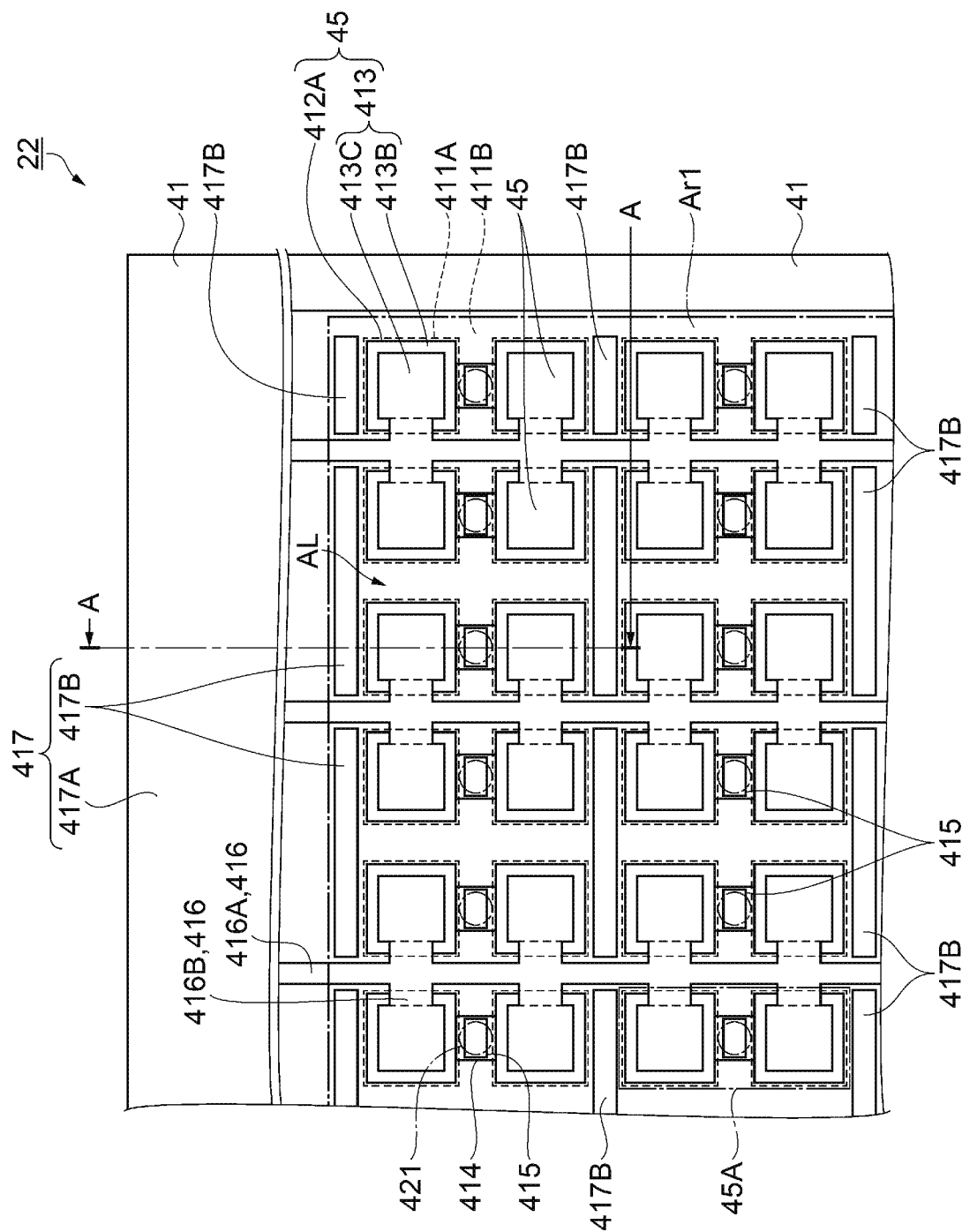
FIG. 3 is a plan view illustrating a schematic configuration of an element substrate in an ultrasonic device according to the first embodiment.
Figure 4:
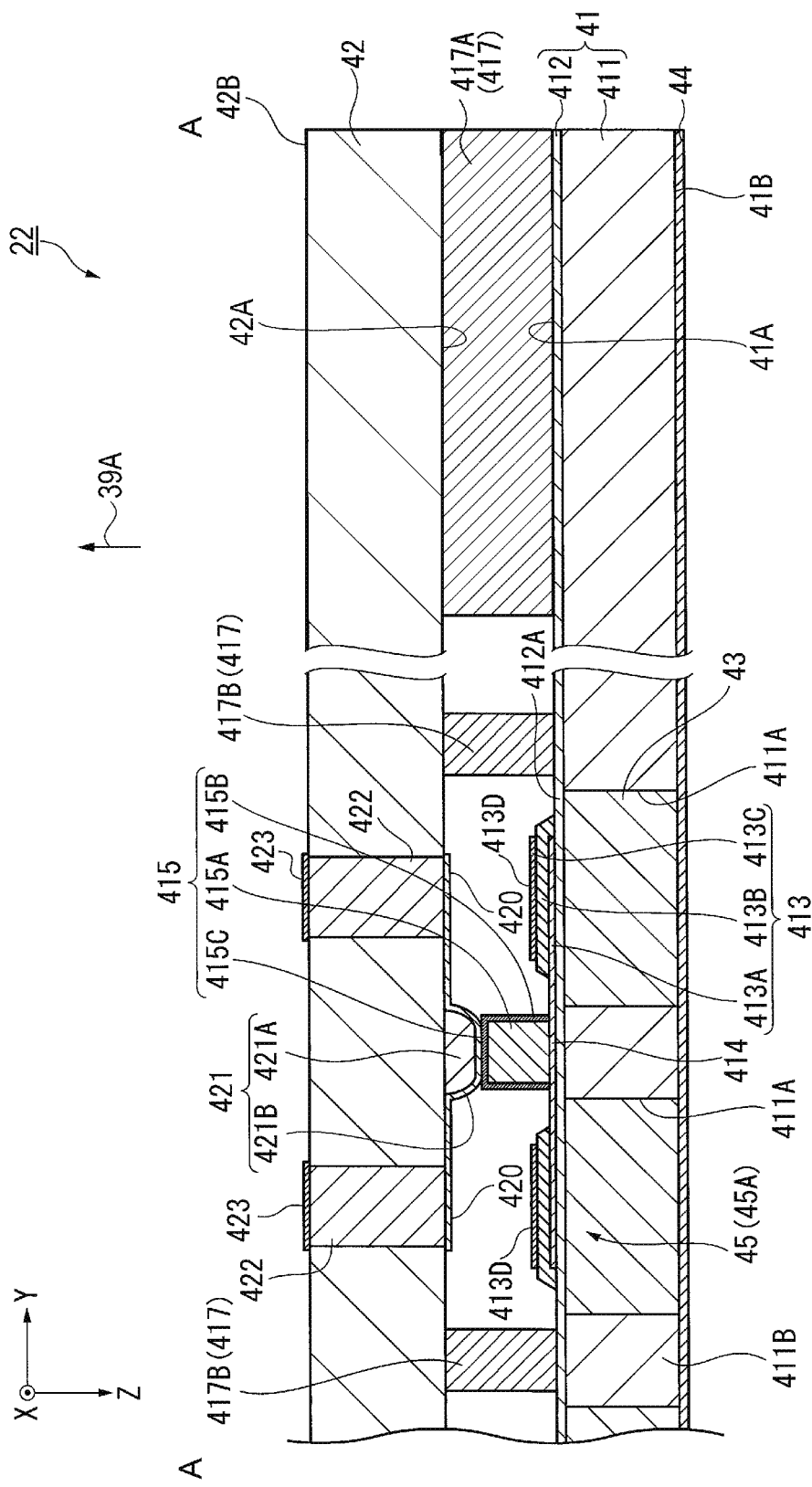
FIG. 4 is a sectional view of the ultrasonic device taken along the line A-A in FIG. 3.
Figure 5:
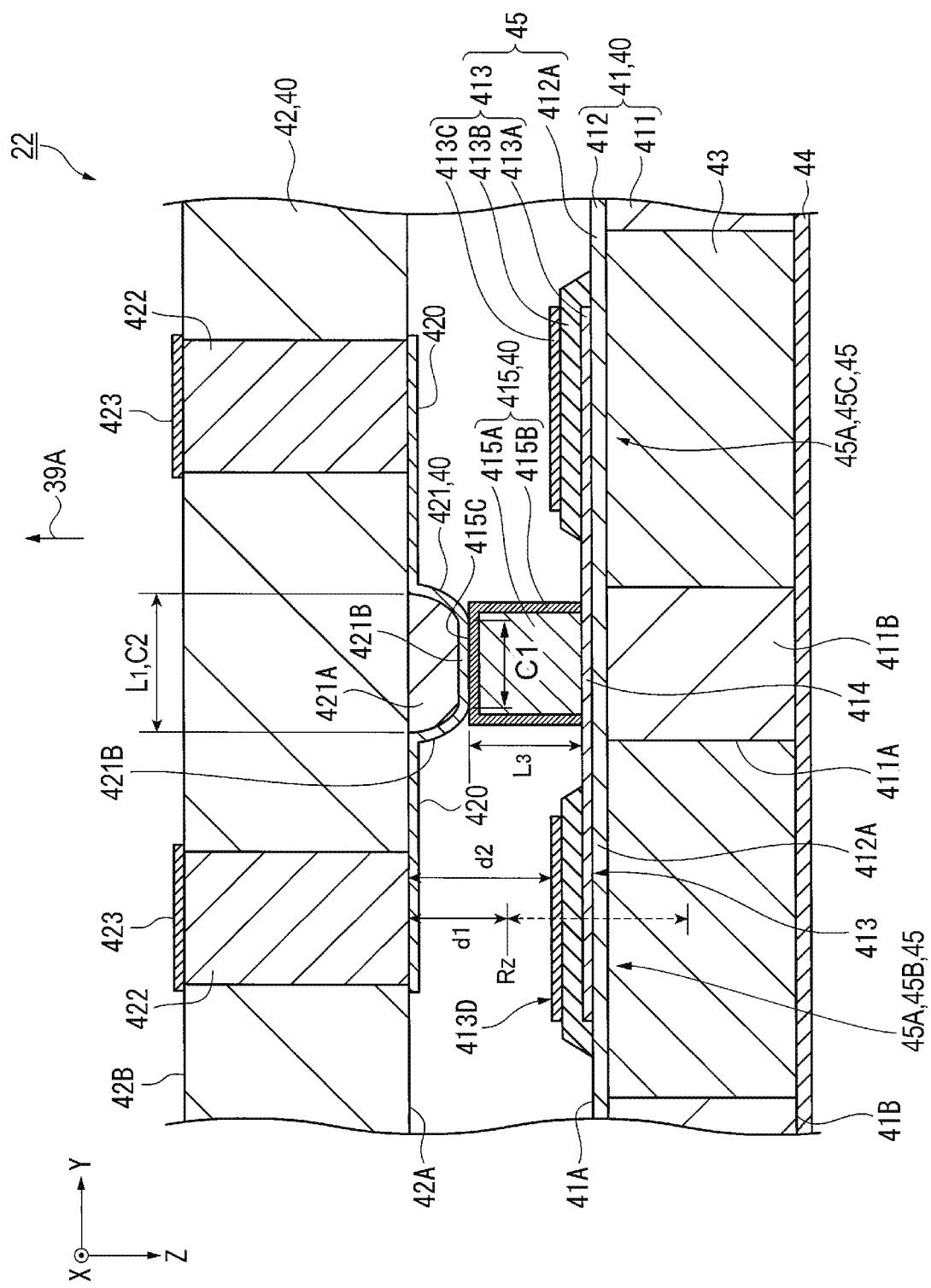
FIG. 5 is a sectional view illustrating a schematic configuration of main portions of the ultrasonic device according to the first embodiment.
Figure 6:
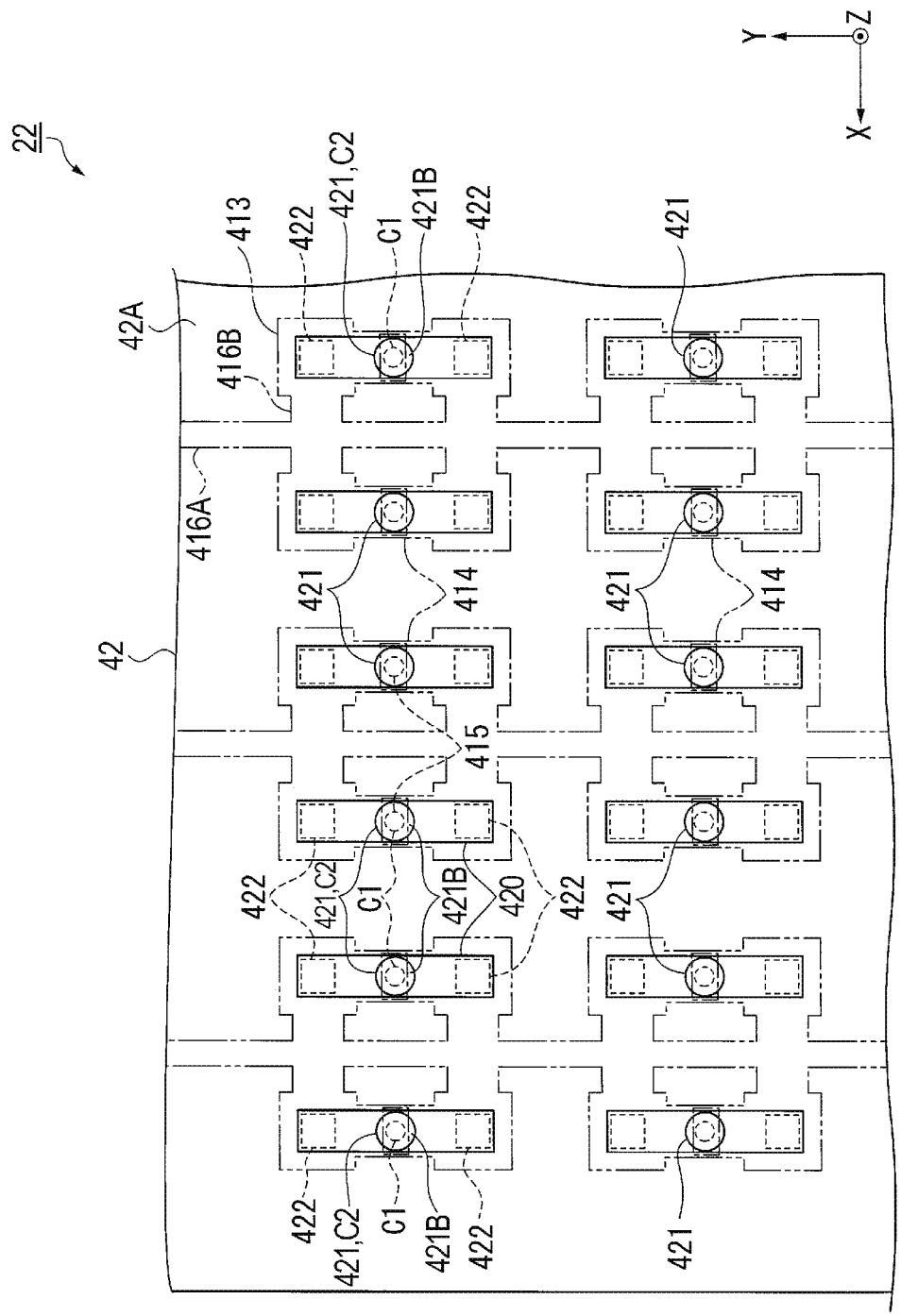
FIG. 6 is a plan view illustrating a schematic configuration of a sealing plate in the ultrasonic device according to the first embodiment.

FIG. 3 is a plan view in which an element substrate 41 of the ultrasonic device 22 is viewed from a protection film 44 side. FIG. 4 is a sectional view of the ultrasonic device 22 taken along the line A-A in FIG. 3. FIG. 5 is a sectional view illustrating a schematic configuration of the periphery of a conductor 421 which will be described later in the ultrasonic device 22. FIG. 6 is a plan view schematically illustrating an ultrasonic transducer 45 viewed from the protection film 44 side.

As illustrated in FIG. 4, the ultrasonic device 22 is configured to include the element substrate 41, the sealing plate 42, an acoustic matching layer 43, and the protection film 44. Among them, the element substrate 41 and the sealing plate 42 are electrically connected to each other via the conductor 421 provided on the sealing plate 42 side and a conduction wiring (not illustrated).

As illustrated in FIG. 3, the element substrate 41 is provided with the ultrasonic transducer 45 as a functional element which transmits and receives ultrasonic waves, and a plurality of ultrasonic transducers 45 are disposed in a matrix along an X direction and a Y direction intersecting (in the present embodiment, orthogonal to) the X direction. An ultrasonic array AL is formed of the plurality of ultrasonic transducers 45.

Configuration of Element Substrate

Referring to FIG. 4 again, the element substrate 41 corresponds to a first substrate, and includes a substrate main body 411, and a vibration film 412 laminated on the substrate main body 411. The element substrate 41 is provided with piezoelectric elements 413 as vibrators, a lower electrode connection line 414, a wiring 415, an upper electrode extraction line 416 (refer to FIG. 3), and bonds 417 on the vibration film 412 on the sealing plate 42 side. The ultrasonic transducer 45 which transmits and receives an ultrasonic wave is formed of a flexible film 412A and the piezoelectric element 413 in a vibration region of the vibration film 412 among the constituent elements. In FIG. 3, in a plan view in which the element substrate 41 is viewed from a substrate thickness direction, a central region of the element substrate 41 is an array region Ar1 in which the ultrasonic array AL formed of a plurality of ultrasonic transducers 45 is provided. The array region Ar1 corresponds to a functional region. The plurality of ultrasonic transducers 45 are disposed in a matrix in the array region Ar1.

In the following description, a surface of the element substrate 41 facing the sealing plate 42 illustrated in FIG. 4 will be referred to as a rear surface 41A corresponding to a first surface, and a surface opposite to the rear surface 41A will be referred to as an operation surface 41B. The ultrasonic transducer 45 is provided on the rear surface 41A of the element substrate 41. A normal direction to the operation surface 41B is substantially the same as the Z direction, and a direction (first direction 39A) from the element substrate 41 toward the sealing plate 42 is substantially parallel to the Z direction.

The substrate main body 411 is, for example, a semiconductor substrate such as Si. An opening 411A corresponding to each ultrasonic transducer 45 is provided in the array region Ar1 in the substrate main body 411. The respective openings 411A are separated by a wall 411B. Each opening 411A is closed by the vibration film 412 provided on an opposite side (−Z side) to the protection film 44 of the substrate main body 411.

The vibration film 412 is formed of, for example, SiO$_2$, or a laminate of SiO$_2$ and ZrO$_2$, and is provided to cover the entire −Z side of the substrate main body 411. In the vibration film 412, a portion closing the opening 411A forms the flexible film 412A which is elastically deformed. A thickness dimension (thickness) of the vibration film 412 is small relative to the substrate main body 411. In a case where the substrate main body 411 is made of Si, and the vibration film 412 is made of SiO$_2$, for example, the substrate main body 411 is subjected to oxidation treatment, and thus the vibration film 412 having a desired thickness dimension (thickness) can be easily formed. In this case, the substrate main body 411 is etched with the vibration film 412 of SiO$_2$ as an etching stopper, and thus the opening 411A can be easily formed.

Each piezoelectric element 413 is provided on the flexible film 412A of the vibration film 412 closing each opening 411A. A single ultrasonic transducer 45 is formed of the flexible film 412A and the piezoelectric element 413. The piezoelectric element 413 is formed of a laminate of a lower electrode 413A, a piezoelectric film 413B, and an upper electrode 413C. Therefore, the ultrasonic transducer 45 includes the piezoelectric element 413 which vibrates in the first direction 39A.

The lower electrode 413A or the upper electrode 413C is configured to include a layer made of one or two or more conductive materials. As such a conductive material, for example, electrode materials such as Au, Al, Cu, Ir, Pt, IrOx, Ti, TiW, and TiOx may be used. In the present embodiment, for example, the lower electrode 413A is formed by laminating a TiW layer (50 nm) and a Cu layer (100 nm) in this order on the vibration film 412.

The piezoelectric film 413B is formed by using, for example, a transition metal oxide having a perovskite structure, more specifically, lead zirconate titanate containing Pb, Ti, and Zr.

A rectangular wave voltage with a predetermined frequency is applied between the lower electrode 413A and the upper electrode 413C in the ultrasonic transducer 45, and thus an ultrasonic wave can be transmitted by causing the flexible film 412A located in the opening region of the opening 411A to vibrate along the Z direction. If the flexible film 412A vibrates due to an ultrasonic wave reflected from a target object, a potential difference occurs in the upper and lower portions of the piezoelectric film 413B. Therefore, the received ultrasonic wave can be detected by detecting the potential difference occurring between the lower electrode 413A and the upper electrode 413C.

In the present embodiment, as illustrated in FIG. 3, among the plurality of ultrasonic transducers 45 disposed along the X direction and the Y direction, two ultrasonic transducers 45 arranged in the Y direction form an ultrasonic transducer group 45A which is a single transmission/reception channel. In other words, the ultrasonic array AL has a two-dimensional array structure in which the ultrasonic transducer groups 45A are disposed at substantially the same interval along the X direction and the Y direction. That is, the ultrasonic array AL is a two-dimensional array formed by arranging a plurality of transmission/reception channels along the X direction and the Y direction.

Here, referring to FIG. 4 again, the respective lower electrodes 413A forming the ultrasonic transducer groups 45A are connected to each other via the lower electrode connection line 414. The lower electrode connection line 414 is integrally formed with the respective lower electrodes 413A, and thus connects the lower electrodes 413A to each other. In other words, the lower electrode connection line 414 is formed by laminating a TiW layer (50 nm) and a Cu layer (100 nm), and has a thickness dimension (thickness) of 150 nm, in the same manner as, for example, the lower electrode 413A. The lower electrode connection line 414 may be provided separately from the lower electrode 413A.

The wiring 415 is provided on the lower electrode connection line 414 configured as mentioned above.

The wiring 415 which is conductive includes a main body 415A and a coating 415B coating the main body 415A. The wiring 415 is disposed at a position which is different from (laterally spaced apart from) that of the ultrasonic transducer 45 of the rear surface 41A and is connected to the ultrasonic transducer 45. As illustrated in FIG. 3, the wiring 415 is formed at a position overlapping the wall 411B in a plan view viewed from the Z direction, and has a substantially rectangular outer shape. As illustrated in FIGS. 4 and 5, the wiring 415 protrudes from the lower electrode connection line 414 toward the sealing plate 42 side so as to be in contact with and electrically connected to the conductor 421 provided on the sealing plate 42 side. In other words, the lower electrode 413A of each ultrasonic transducer 45 is electrically connected to the conductor 421 on the sealing plate 42 side via the lower electrode connection line 414 and the wiring 415. A mounting structure 40 is configured to include at least the element substrate 41, the wiring 415, the sealing plate 42, and the conductor 421.

The main body 415A is formed by using a conductive metal material. The main body 415A is disposed at a position overlapping the wall 411B on the lower electrode connection line 414 in a plan view viewed from the Z direction. The main body 415A protrudes toward the sealing plate 42 side from the element substrate 41. The main body 415A is formed by depositing Cu which is the metal material on the lower electrode connection line 414, for example, according to an electroplating method. The main body 415A is formed to have, for example, 10 μm as a dimension (width dimension) in the Y direction and a dimension (height dimension) in the Z direction. A width dimension of the wall 411B is, for example, about 20 μm.

The coating 415B is formed by using a conductive metal material, and is formed to cover a surface of the main body 415A. The coating 415B is formed by laminating a Ni layer (50 nm) and an Au layer (100 nm) from the main body 415A side. The coating 415B is formed by using a material such as Au having a relatively high electric conductivity, and thus it is possible to reduce contact resistance with the conductor 421.

The coating 415B is not limited to the configuration in which the Ni layer (50 nm) and an Au layer (100 nm) are laminated, and may be formed by using various conductive materials.

As illustrated in FIG. 5, an end surface (hereinafter, also referred to as an distal end 415C) of the wiring 415 on the sealing plate 42 side is located further toward the sealing plate 42 side than an end surface (hereinafter, also referred to as an distal end 413D) on the −Z side of the piezoelectric element 413 of the ultrasonic transducer 45. In the present embodiment, the distal end 415C is located further toward the sealing plate 42 side than a −Z side end part Rz of a vibration range of the ultrasonic transducer 45.

The distal end 415C is a location where the wiring 415 is connected to the conductor 421. The distal end 415C is located further toward the sealing plate 42 side than the vibration range of the piezoelectric element 413 in the first direction 39A. Therefore, the wiring 415 and the conductor 421 are connected to each other closer to the sealing plate 42 side than the vibration range of the piezoelectric element 413 in the first direction 39A. In this configuration, the conductor 421 can be disposed outside a drive range of the piezoelectric element 413. Consequently, it is possible to further prevent the conductor 421 from hindering vibration of the piezoelectric element 413, and thus to appropriately drive the piezoelectric element 413.

In the wiring 415, a ratio of a dimension (height dimension) in the Z direction to a minimum dimension (a width dimension which is a dimension in the Y direction in the present embodiment) in an XY section of the wiring 415, that is, an aspect ratio is preferably 0.1 or more and 5 or less, and is more preferably 0.1 or more and 1 or less. Consequently, it is possible to prevent the wiring 415 from being deformed or inclined by pressure from the conductor 421, and thus to improve the reliability of electrical connection.

A planar shape of the wiring 415 in a plan view viewed from the Z direction is not limited to a rectangular shape, and may be a circular shape, an elliptical shape, and various polygonal shapes. A direction of the XY section of the wiring 415 corresponds to a surface direction of (a plane of) the rear surface 41A.

As illustrated in FIG. 3, each upper electrode 413C of the ultrasonic transducer 45 is connected to a terminal (not illustrated) at an outer surface 42B illustrated in FIG. 5 via the upper electrode extraction line 416 and a wiring (not illustrated). Referring to FIG. 3 again, the upper electrode extraction line 416 which is made of a conductive material is integrally formed with, for example, the upper electrode 413C, and includes a plurality of extractions 416A disposed along the Y direction and connectors 416B. The connector 416B connects the extraction 416A to the upper electrode 413C.

For example, each of the extractions 416A is disposed between the odd-numbered and even-numbered ultrasonic transducer groups 45A, for example, when counted along the X direction, and is connected to the upper electrode 413C of the ultrasonic transducer group 45A via the connector 416B.

Each upper electrode 413C is connected to a ground circuit (not illustrated) of the circuit substrate 23 via a wiring formed on the sealing plate 42, and is set to a reference potential.

The bond 417 bonds the element substrate 41 to the sealing plate 42 configured as described above. The bond 417 includes a first bond 417A, and a second bond 417B. The first bond 417A is disposed along the outer edge of the element substrate 41. The second bond 417B bonds the element substrate 41 and the sealing plate 42 to each other in the array region Ar1. The second bond 417B is disposed along the ultrasonic transducer 45.

The bond 417 is formed by using a material which can bond the element substrate 41 to the sealing plate 42, for example, various adhesives or a resin material such as a photosensitive resin material (photoresist). In the present embodiment, the bond 417 is formed by using a photosensitive resin material. Consequently, the bond 417 can be formed at a desired position in a desired shape.

As mentioned above, the second bond 417B bonds the element substrate 41 and the sealing plate 42 to each other in the array region Ar1 in which the ultrasonic transducers 45 are formed. Consequently, for example, even in a case where a plurality of conductors 421 and the wirings 415 are formed in the array region Ar1, that is, a plurality of connection positions are present, the uniformity of a distance between the element substrate 41 and the sealing plate 42 in the array region Ar1 can be improved, and thus the connection reliability at each connection position can be improved.

As illustrated in FIGS. 3 and 4 as an example, the second bonds 417B are disposed along the X direction at the positions overlapping the walls 411B on the surface of the vibration film 412 on the sealing plate 42 side. The first bond 417A and the second bond 417B are formed on the vibration film 412, that is, in the region in which the upper electrode extraction line 416 and the like are not formed. Consequently, thickness dimensions (thicknesses) of the first bond 417A and the second bond 417B can be made uniform regardless of a formation position.

The second bond 417B is disposed between the extractions 416A of the upper electrode extraction line 416. The second bonds 417B are disposed at positions interposing each wiring 415 in the Y direction. In this configuration, the second bonds 417B can be disposed such that distances between the respective wirings 415 and the second bonds 417B are the same as each other. Therefore, the stress from the second bonds 417B can be substantially uniformly applied to the respective connection positions of the wirings 415.

The second bond 417B is not limited to the configuration of being directly provided on the vibration film 412, and may be disposed on the extraction 416A of the upper electrode extraction line 416 along the X direction.

The second bond 417B is formed in at least the array region Ar1, and thus the connection reliability between the wiring 415 and the conductor 421 can be improved compared with a case where only the first bond 417A is provided.

Configuration of Sealing Plate

The sealing plate 42 illustrated in FIGS. 4 to 6 corresponds to a second substrate and is provided to reinforce the strength of the element substrate 41.

The sealing plate 42 is formed of, for example, a semiconductor substrate, and is bonded to the element substrate 41 via the bonds 417. A material or a thickness of the sealing plate 42 influences frequency characteristics of the ultrasonic transducer 45, and is thus preferably set on the basis of a center frequency of transmitted and received ultrasonic waves.

The sealing plate 42 is provided with the conductor 421, a through-hole connection line 420, a through-electrode 422, and a lower electrode wire 423. A surface of the sealing plate 42 facing the rear surface 41A of the element substrate 41, that is, a surface on the element substrate 41 side will be referred to as an inner surface 42A corresponding to a second surface.

Configuration of Conductor

The conductor 421 is illustrated in FIGS. 4 to 6. The conductor 421 is provided on the inner surface 42A of the sealing plate 42, and is in pressure and close contact with the wiring 415 provided on the element substrate 41, and is electrically connected to the wiring 415. The conductor 421 is connected to the ultrasonic transducer 45 via the wiring 415. The conductor 421 includes a resin core 421A corresponding to a resin part, and a conductive film 421B as a conductive part (cap) which covers the resin core 421A. A through-hole connection line 420 electrically connects the conductive film 421B to the through-electrode 422. The conductive film 421B and the through-hole connection line 420 may be a continuous conductive film.

The resin core 421A is provided on the inner surface 42A at a position overlapping (aligned with) the wiring 415 on the rear surface 41A as illustrated in FIG. 5, and protrudes from the inner surface 42A toward the element substrate 41. The resin core 421A is made of an elastic resin material, and is formed in a substantially hemispherical shape by thermally melting a resin material disposed on the inner surface 42A as will be described later. The resin core 421A may be formed in a substantially trapezoidal shape (a state in which corners of a trapezoidal are rounded) according to the kind of resin material, or a temperature condition in thermal melting.

A photosensitive resin material (photoresist) is preferably used as a material forming the resin core 421A. In this case, the resin core 421A may be formed in a desired shape at a desired position. As a material forming the resin core 421A, not only a photosensitive resin material, but also various elastic resin materials, for example, polyimide resin, acrylic resin, phenol resin, epoxy resin, silicone resin, and modified polyimide resin may be used.

The conductive film 421B is made of a conductive material, and coats the resin core 421A. The through-hole connection line 420 is connected to the conductive film 421B, extends to a formation position of the through-electrode 422 along the Y direction, and is connected to the through-electrode 422. A thickness of the conductive film 421B is much smaller than a thickness of the resin core 421A, and thus the conductive film 421B can be deformed according to elastic deformation of the resin core 421A.

As a conductive material forming the conductive film 421B, Au, Ag, TiW, Cu, Ni, Pd, Al, Cr, Ti, W, NiCr, or a lead-free solder may be used. In the present embodiment, for example, the conductive film 421B is formed by laminating a TiW layer (50 nm) and an Au layer (100 nm) in this order from the inner surface 42A side. In this configuration, the Au layers located on the respective surfaces of the conductive film 421B and the coating 415B of the wiring 415 can be bonded to each other through diffusion bonding. Consequently, the reliability of electrical connection between the conductor 421 and the wiring 415 can be further improved.

As illustrated in FIGS. 4 and 5, the conductor 421 configured as mentioned above is in pressure contact with the distal end 415C of the wiring 415, and thus the resin core 421A and the conductive film 421B are elastically deformed. In this case, the +Z side end part of the conductor 421 is deformed along the distal end 415C, and is thus in close contact with the distal end 415C in a first connection region C1 (refer to FIG. 6). As mentioned above, since the resin core 421A and the conductive film 421B are elastic, the conductor 421 and the distal end 415C can be placed in close contact with each other, and thus it is possible to improve the reliability of electrical connection between the conductor 421 and the wiring 415.

As illustrated in FIG. 5, here, a connection position between the conductor 421 and the wiring 415 is located further toward the sealing plate 42 side than the distal end 413D of the piezoelectric element 413 in the same manner as the distal end 415C of the wiring 415. In other words, the shortest distance (a distance at a location where a distance between the distal end 413D of the piezoelectric element 413 and the sealing plate 42 is shortest) between the distal end 413D of the piezoelectric element 413 and the sealing plate 42 is longer than a distance (a distance at a location where a distance between the connection position and the sealing plate 42 is longest) between the connection position where the conductor 421 and the wiring 415 are connected to each other and the sealing plate 42. That is, the shortest distance between the distal end 413D of the piezoelectric element 413 and the inner surface 42A of the sealing plate 42 is longer than a distance between the connection position where the conductor 421 is connected to the wiring 415 and the inner surface 42A of the sealing plate 42. In the present embodiment, the connection position is located further toward the sealing plate 42 side than the −Z side end part Rz of the vibration range of the ultrasonic transducer 45. Therefore, the shortest distance between the ultrasonic transducer 45 or the piezoelectric element 413 and the sealing plate 42 is longer than a distance from the position where the wiring 415 is connected to the conductor 421 to the sealing plate 42.

Consequently, for example, even if a position difference occurs in the conductor 421 when wiring connection is performed around the ultrasonic transducer 45, it is possible to suppress interference between the ultrasonic transducer 45 and the conductor 421. Therefore, it is possible to easily perform wiring connection between the element substrate 41 and the sealing plate 42. The conductor 421 is in contact with the distal end 415C of the wiring 415, and thus wiring connection between the element substrate 41 and the sealing plate 42 can be performed. Therefore, as described above, a connection position is located further toward the sealing plate 42 side than the piezoelectric element 413, and thus wiring connection can be easily performed. Since a connection position can be set according to a dimension of the wiring 415, it is possible to easily adjust a connection position according to the piezoelectric element 413.

A region in which the wiring 415 is connected to the conductor 421 is referred to as the first connection region C1. A region in which the conductor 421 is bonded to the sealing plate 42 is referred to as a second connection region C2. The conductor 421 has the conductive film 421B which is curved toward the sealing plate 42 from the first connection region C1 (in a case where, the distal end 415C of the wiring 415 is flat, the connection position where the conductor 421 is connected to the wiring 415 is the first connection region C1 in a plan view) to the outside in the surface direction (a surface direction of the XY plane) of the rear surface 41A. That is, the conductive film 421B is curved to be separated from the piezoelectric element 413 toward the piezoelectric element 413 side along the XY plane. In other words, an area of the region (second connection region C2) in which the conductor 421 is bonded to the sealing plate 42 is larger than an area of the region (first connection region C1) in which the wiring 415 is connected to the conductor 421.

In this configuration, a distance between the conductor 421 and the ultrasonic transducer 45 in a plane intersecting the first direction 39A can be increased toward the element substrate 41 on which the ultrasonic transducer 45 is provided from the sealing plate 42. Consequently, it is possible to further suppress interference between the ultrasonic transducer 45 and the conductor 421. The conductor 421 and the ultrasonic transducer 45 can be disposed to be closer to each other in a plan view viewed from the first direction 39A.

The resin core 421A has a substantially hemispherical shape when not undergoing elastic deformation, and is provided to protrude from the inner surface 42A on the sealing plate 42. An end surface (a surface of which the resin core 421A is in contact with the sealing plate 42) of the resin core 421A on the inner surface 42A side is substantially circular. In a case where a diameter (that is, the maximum dimension or the maximum diameter) of the end surface of the resin core 421A is indicated by $L_1$, a distance d1 from the sealing plate 42 to the −Z side end part Rz of the vibration range of the ultrasonic transducer 45 satisfies the following Expression (1). Consequently, it is possible to further suppress interference between the ultrasonic transducer 45 and the conductor 421. In other words, in a case where the conductor 421 is not elastically deformed, a tip end thereof on the +Z side is located at a distance of about $L_1/2$ from the sealing plate 42. Therefore, since the distance d1 satisfies the following Expression (1), the conductor 421 can be disposed outside the drive range of the ultrasonic transducer 45. As a result, it is possible to further suppress interference between the conductor 421 and the ultrasonic transducer 45.

Actually, the sealing plate 42 is bonded to the element substrate 41, and then the conductor 421 is brought into contact with the wiring 415. Since the conductor 421 is pressed against the wiring 415 so as to be elastically deformed, a distance from the sealing plate 42 to the tip end of the conductor 421 on the +Z side is smaller than $L_1/2$. Therefore, in a case where the −Z side end part Rz of the vibration range is located further toward the element substrate 41 side than the distal end 415C, a distance d2 between the distal end 413D of the piezoelectric element 413 and the sealing plate 42 during drive stoppage satisfies the following Expression (2), and thus it is also possible to suppress interference between the ultrasonic transducer 45 and the conductor 421. In other words, the conductor 421 may not be brought into contact with the ultrasonic transducer 45 before bonding.

$$d1 > L_1/2 \quad (1)$$

$$d2 > L_1/2 \quad (2)$$

The piezoelectric element 413 vibrates along the first direction 39A in the ultrasonic transducer 45. Also in this configuration, it is possible to suppress interference between the conductor 421 and the ultrasonic transducer 45. In other words, it is possible to further prevent the conductor 421 from hindering vibration of the piezoelectric element 413, and thus to appropriately drive the piezoelectric element 413.

The ultrasonic transducer 45 includes the flexible film 412A formed on the element substrate 41 and the piezoelectric element 413 provided on the flexible film 412A. In this configuration, as described above, it is possible to further prevent the conductor 421 from hindering vibration of the piezoelectric element 413, and thus to appropriately drive the ultrasonic transducer 45.

A pair of ultrasonic transducers 45 are provided with the wiring 415 interposed therebetween on the Y direction side of the wiring 415. The ultrasonic transducer 45 on the −Y direction side of the wiring 415 will be referred to as a first ultrasonic transducer 45B as a first functional element, and the ultrasonic transducer 45 on the +Y direction side of the wiring 415 will be referred to as a second ultrasonic transducer 45C as a second functional element. As mentioned above, the ultrasonic transducers 45 include the first ultrasonic transducer 45B and the second ultrasonic transducer 45C.

The wiring 415 is connected to the first ultrasonic transducer 45B and the second ultrasonic transducer 45C. The wiring 415 is disposed between the first ultrasonic transducer 45B and the second ultrasonic transducer 45C in a plan view from the first direction 39A.

In this configuration, a single wiring 415 is connected to the first ultrasonic transducer 45B and the second ultrasonic transducer 45C. Therefore, an area of the wiring 415 can be reduced compared with a case where the wiring 415 for the first ultrasonic transducer 45B only and the wiring 415 for the second ultrasonic transducer 45C only are provided. As a result, the first ultrasonic transducer 45B, the second ultrasonic transducer 45C, and the wiring 415 can be disposed on the element substrate 41 with higher density.

In the first direction 39A, the resin core 421A at the position overlapping the connection region between the conductor 421 and the wiring 415 is thicker than the conductive film 421B. The resin core 421A is thicker than the conductive film 421B as mentioned above, and thus the conductor 421 can be easily deformed. Consequently, the stress, when the wiring 415 is brought into contact with the conductor 421, can be alleviated, and thus it is possible to suppress the occurrence of distortion of the element substrate 41 and the sealing plate 42. Since a thickness of the conductive film 421B is small, and thus the resin core 421A is easily deformed, for example, even if an error occurs in a thickness of the wiring 415, the wiring 415 can be brought into close contact with the conductor 421 due to deformation of the resin core 421A, and thus it is possible to improve the connection reliability.

Configurations of Through-Electrode and Lower Electrode Wire

As illustrated in FIGS. 4 to 6, a pair of through-electrodes 422 are provided at positions with the resin core 421A interposed therebetween along the Y direction, and may be, for example, a Si through-electrode (through-silicon via: TSV), or may employ a configuration in which a through-hole is filled with a conductive material. The lower electrode wire 423 is individually formed with respect to each through-electrode 422 on the −Z side surface (hereinafter, referred to as an outer surface 42B) of the sealing plate 42. The lower electrode wire 423 is connected to the through-electrode 422, and is connected to the circuit substrate 23 via a wiring (not illustrated) formed along the outer surface 42B.

At least one through-electrode 422 may be formed, and three or more through-electrodes may be formed. A position where the through-electrode 422 is formed is not limited to the above-described position, and may be formed on, for example, the +X side or −X side of the resin core 421A in a plan view viewed from the Z direction.

Configurations of Acoustic Matching Layer and Protection Film

The acoustic matching layer 43 is disposed on the ultrasonic transducer 45 on the operation surface 41B side. In the present embodiment, the acoustic matching layer 43 fills the opening 411A formed on the operation surface 41B side.

The protection film 44 is provided on the element substrate 41 and the acoustic matching layer 43, so as to protect the element substrate 41 and the acoustic matching layer 43. As illustrated in FIG. 1, the protection film 44 is exposed to the outside from the sensor window 21B of the case 21, and is brought into contact with a living body surface during ultrasonic measurement.

The acoustic matching layer 43 or the protection film 44 causes an ultrasonic wave transmitted from the ultrasonic transducer 45 to propagate through a living body which is a measurement target with high efficiency, and causes an ultrasonic wave reflected inside the living body to propagate through the ultrasonic transducer 45 with high efficiency. Thus, acoustic impedance of the acoustic matching layer 43 and the protection film 44 is set to a value similar to acoustic impedance of the living body. The element substrate 41, the wiring 415, the sealing plate 42, and the conductor 421 are stored in the case 21.

Configuration of Circuit Substrate

As illustrated in FIG. 2, the circuit substrate 23 is provided with a driver circuit or the like which is bonded to the ultrasonic device 22 so as to control the ultrasonic transducer 45. The circuit substrate 23 includes a selection circuit 231, a transmission circuit 232, and a reception circuit 233.

In the present embodiment, a wiring connected to the upper electrode 413C which is a common electrode of the ultrasonic transducers 45 is connected to, for example, a ground circuit in the circuit substrate 23. Consequently, the upper electrode 413C is set to a predetermined common potential (for example, 0 potential).

The selection circuit 231 is connected to the lower electrode wire 423 extracted from each ultrasonic transducer group 45A. The selection circuit 231 switches between connection states such as transmission connection for connecting the ultrasonic device 22 to the transmission circuit 232 and reception connection for connecting the ultrasonic device 22 to the reception circuit 233 under the control of the control device 10.

The transmission circuit 232 outputs a transmission signal for transmitting ultrasonic waves to the ultrasonic device 22 via the selection circuit 231 when a connection state is switched to the transmission connection under the control of the control device 10.

The reception circuit 233 outputs a received signal which is input from the ultrasonic device 22 via the selection circuit 231, to the control device 10 when a connection state is switched to the reception connection under the control of the control device 10. The reception circuit 233 is configured to include, for example, a low-noise amplification circuit, a voltage controlled alternator, a programmable gain amplifier, a low-pass filter, and an A/D converter, performs various signal processes such as conversion of the received signal into a digital signal, removal of a noise component, and amplification to a desired signal level, and then outputs the processed received signal to the control device 10.

Configuration of Control Device

As illustrated in FIG. 2, the control device 10 corresponds to a controller, and is configured to include, for example, an operation unit 11, a display unit 12, a storage unit 13, and a calculation unit 14. The control device 10 may employ, for example, a terminal device such as a tablet terminal, a smart phone, or a personal computer, and may be a dedicated terminal device for operating the ultrasonic probe 2. The control device 10 also controls the ultrasonic transducer 45, the piezoelectric element 413, or the like.

The operation unit 11 is a user interface (UI) for a user to operate the ultrasonic measurement apparatus 1, and may be formed of, for example, a touch panel provided on the display unit 12, operation buttons, a keyboard, and a mouse.

The display unit 12 is formed of, for example, a liquid crystal display, and displays an image.

The storage unit 13 stores various programs or various pieces of data for controlling the ultrasonic measurement apparatus 1.

The calculation unit 14 is formed of, for example, a calculation circuit such as a central processing unit (CPU) and a storage circuit such as a memory. The calculation unit 14 reads various programs stored in the storage unit 13 and executes the programs so as to control processes for causing the transmission circuit 232 to generate and output a transmission signal, and to perform control for setting of a frequency of a reception signal or gain setting in the reception circuit 233.

Manufacturing Method of Ultrasonic Device

Hereinafter, a description will be made of a manufacturing method of the above-described ultrasonic device 22.

Figure 7:
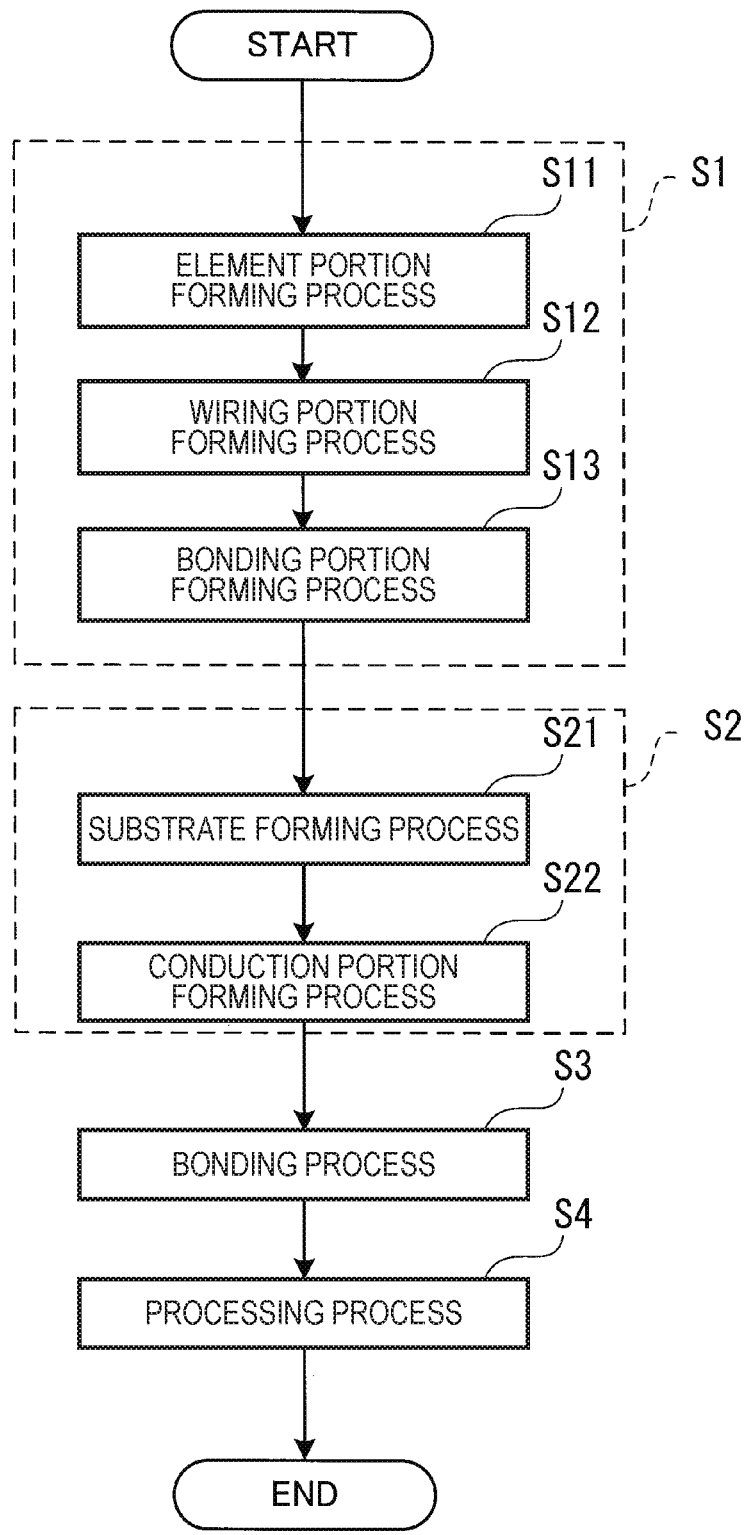
FIG. 7 is a flowchart illustrating an example of a manufacturing method of the ultrasonic device according to the first embodiment.
Figure 8:
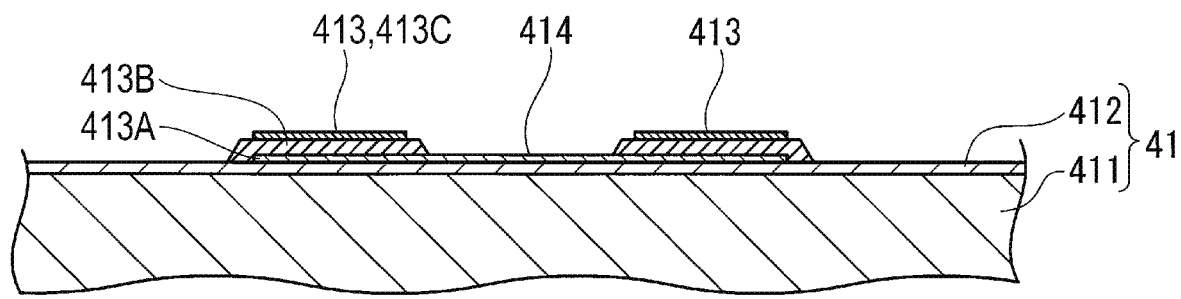
FIG. 8 is a sectional view schematically illustrating an example of a manufacturing process of the ultrasonic device according to the first embodiment.

FIG. 7 is a flowchart illustrating an example of a manufacturing method of the ultrasonic device 22. FIG. 8 to are diagrams schematically illustrating manufacturing processes of the ultrasonic device 22.

In order to manufacture the ultrasonic device 22, as illustrated in FIG. 7, an element substrate forming process S1, a sealing plate forming process S2, a bonding process S3, and a processing process S4.

FIGS. 8 to 23 schematically illustrate sections in the vicinity of the ultrasonic transducer group 45A illustrated in FIG. 4.

Element Substrate Forming Process

As illustrated in FIG. 8, in the element substrate forming process S1, first, for example, the vibration film 412, the piezoelectric elements 413, the lower electrode connection line 414, and the upper electrode extraction line 416 (not illustrated) are formed on the substrate main body 411 made of Si (step S11: element portion forming process). In step S11, a film of Zr is formed on a film of $SiO_2$ which is formed by performing thermal oxidation treatment on the substrate main body 411, and thermal oxidation treatment is further performed so as to form a layer of $ZrO_2$ and thus to form the vibration film 412. The lower electrode 413A, the piezoelectric film 413B, and the upper electrode 413C are formed on the vibration film 412, and thus the piezoelectric element 413 is formed. The lower electrode connection line 414 is formed when the lower electrode 413A is formed, and the upper electrode extraction line 416 is formed when the upper electrode 413C is formed. Specifically, first, an electrode material formed as a film on the vibration film 412 through, for example, sputtering is patterned, and thus the lower electrode 413A and the lower electrode connection line 414 are formed. Thereafter, the piezoelectric film 413B is formed on the lower electrode 413A. After the piezoelectric film 413B is formed, the upper electrode 413C and the upper electrode extraction line 416 are formed in the same manner as the lower electrode 413A and the lower electrode connection line 414.

Figure 9:
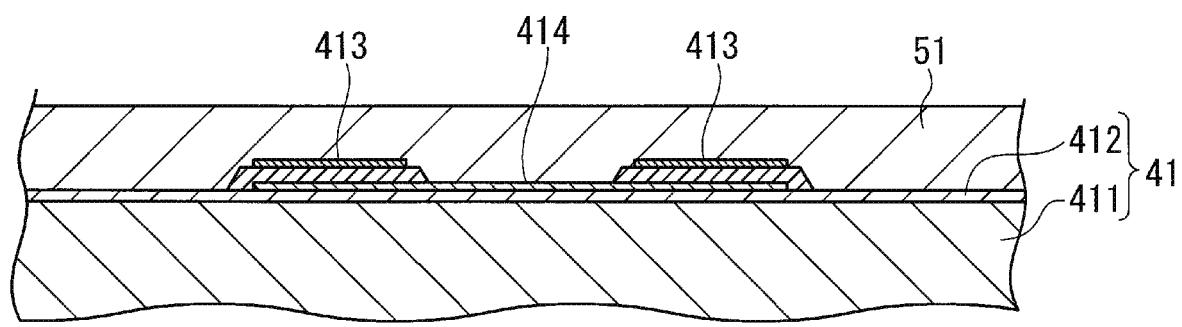
FIG. 9 is a sectional view schematically illustrating an example of a manufacturing process of the ultrasonic device according to the first embodiment.
Figure 10:
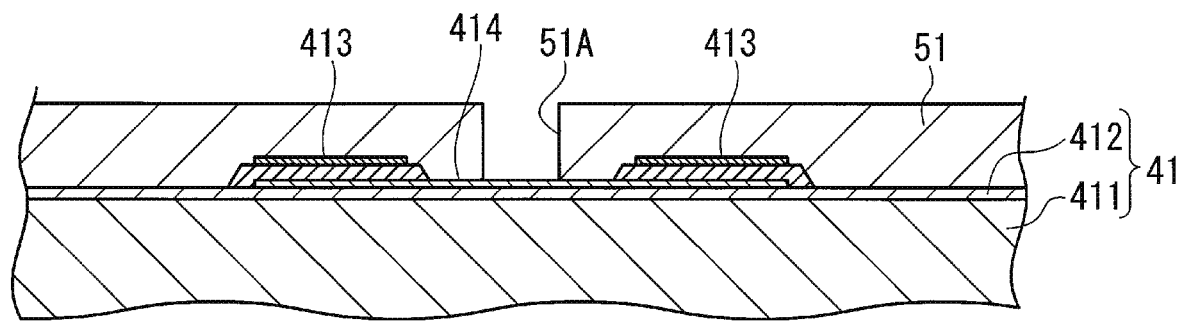
FIG. 10 is a sectional view schematically illustrating an example of a manufacturing process of the ultrasonic device according to the first embodiment.
Figure 11:
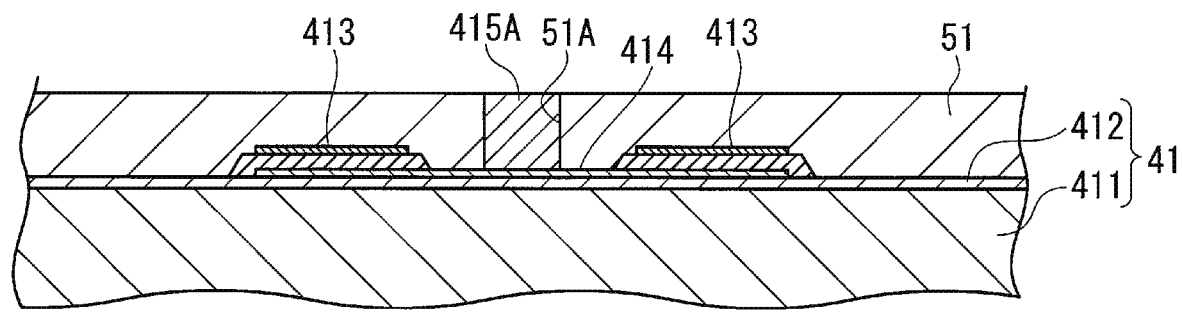
FIG. 11 is a sectional view schematically illustrating an example of a manufacturing process of the ultrasonic device according to the first embodiment.
Figure 12:
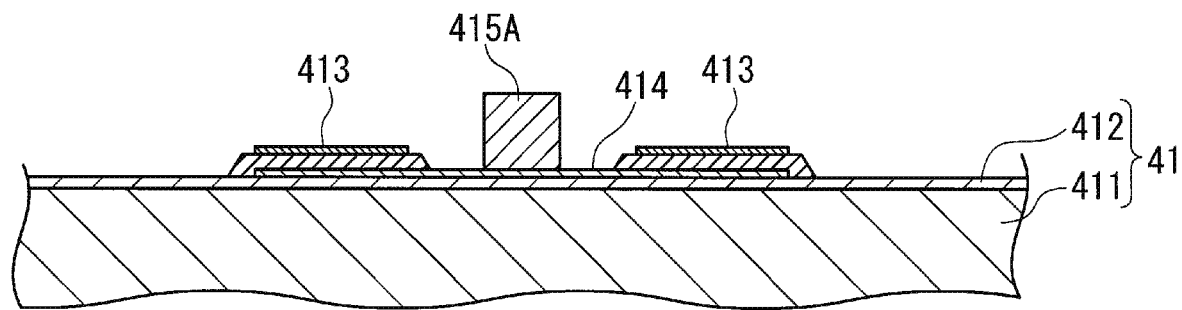
FIG. 12 is a sectional view schematically illustrating an example of a manufacturing process of the ultrasonic device according to the first embodiment.
Figure 13:
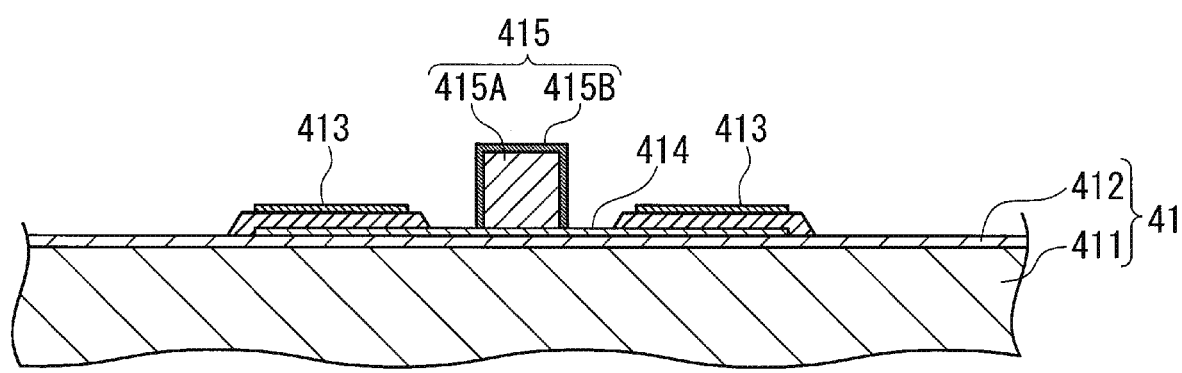
FIG. 13 is a sectional view schematically illustrating an example of a manufacturing process of the ultrasonic device according to the first embodiment.

Next, as illustrated in FIG. 7, the wiring 415 is formed on the lower electrode connection line 414 (step S12: wiring forming process). In step S12, as illustrated in FIG. 9, a photosensitive resin layer 51 is formed. In this case, a thickness of the photosensitive resin layer 51 is adjusted such that a thickness dimension (thickness) of the photosensitive resin layer 51 on the lower electrode connection line 414 is a thickness dimension (thickness) of the main body 415A of the wiring 415. In the present embodiment, the photosensitive resin layer 51 is formed to have a thickness of, for example, 10 μm by using a positive photoresist. The photosensitive resin layer 51 is exposed and developed, as illustrated in FIG. 10, the photosensitive resin layer 51 at the formation position of the main body 415A is removed, and a mask pattern having an opening 51A at the formation position is formed. As illustrated in FIG. 11, the main body 415A is formed by depositing Cu on the lower electrode connection line 414 in the opening 51A according to, for example, an electroplating method, and, as illustrated in FIG. 12, the photosensitive resin layer 51 is removed. Thereafter, as illustrated in FIG. 13, the coating 415B is formed on a surface of the main body 415A according to, for example, an electroless plating method. In the present embodiment, a Ni layer having a thickness dimension (thickness) of 50 nm and an Au layer having a thickness dimension (thickness) of 100 nm are laminated in this order.

Figure 14:
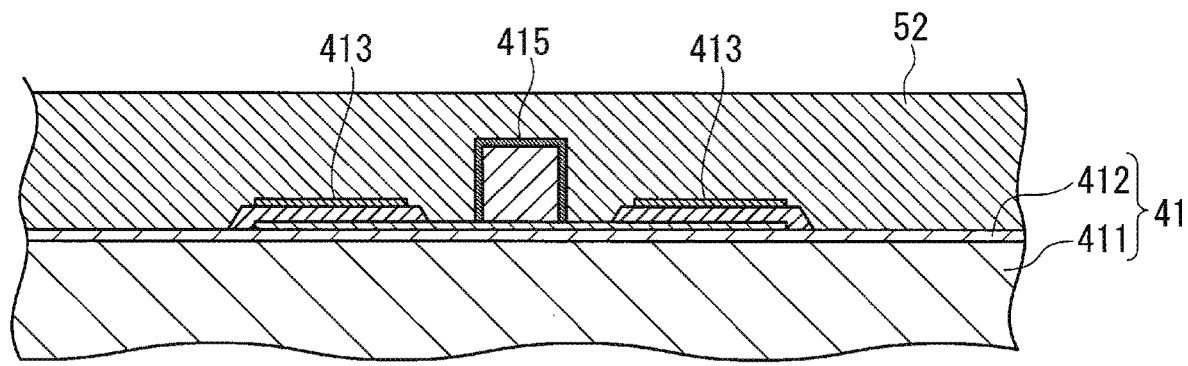
FIG. 14 is a sectional view schematically illustrating an example of a manufacturing process of the ultrasonic device according to the first embodiment.
Figure 15:
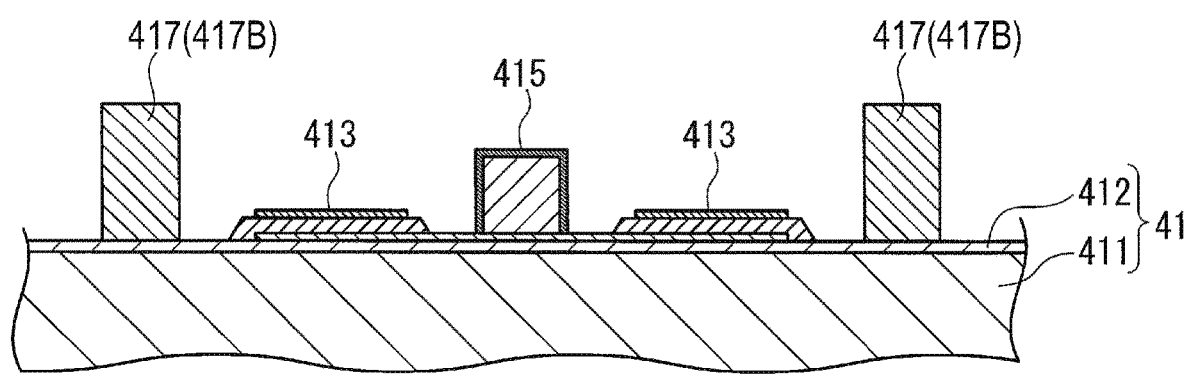
FIG. 15 is a sectional view schematically illustrating an example of a manufacturing process of the ultrasonic device according to the first embodiment.

Next, as illustrated in FIG. 7, the bonds 417 are formed on the element substrate 41 (step S13: bond forming process). In step S13, as illustrated in FIG. 14, for example, a photosensitive resin layer 52 for forming the bonds 417 is formed on the element substrate 41. In this case, a thickness of the photosensitive resin layer 52 is adjusted such that a thickness dimension (thickness) of the photosensitive resin layer 52 is a thickness dimension (thickness) of the bond 417 at a formation position of the bond 417. In the present embodiment, the bond 417 is formed on the vibration film 412 at the respective formation positions, and thus thickness dimensions (thicknesses) are the same as each other. Thus, a surface of the photosensitive resin layer 52 may be formed to be flat, and a thickness is easily adjusted. The photosensitive resin layer 52 is formed to have a thickness of 22 μm and a width (the width in the Y direction illustrated in FIG. 4) of 10 μm at the formation position by using, for example, a negative photoresist. The photosensitive resin layer 52 is exposed and developed such that the bonds 417 are formed as illustrated in FIG. 15.

Sealing Plate Forming Process

Figure 16:
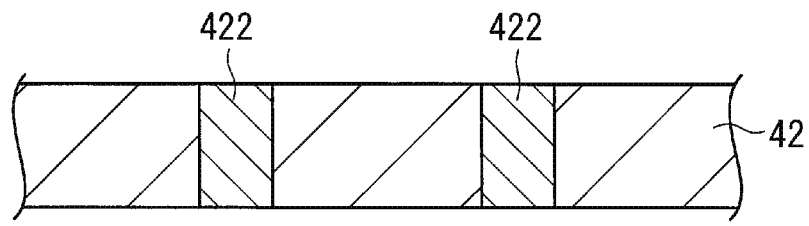
FIG. 16 is a sectional view schematically illustrating an example of a manufacturing process of the ultrasonic device according to the first embodiment.

Next, as illustrated in FIG. 7, the sealing plate forming process S2 is performed. In step S2, as illustrated in FIG. 16, first, the sealing plate 42 provided with the through-electrodes 422 is formed (step S21: substrate forming process (refer to FIG. 7)).

Figure 17:
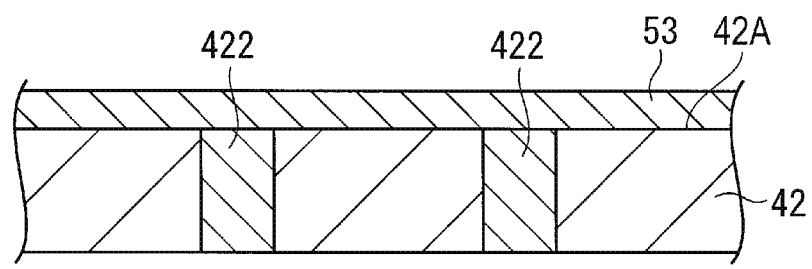
FIG. 17 is a sectional view schematically illustrating an example of a manufacturing process of the ultrasonic device according to the first embodiment.
Figure 18:
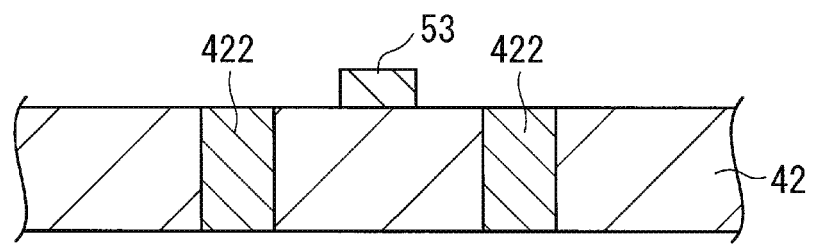
FIG. 18 is a sectional view schematically illustrating an example of a manufacturing process of the ultrasonic device according to the first embodiment.
Figure 19:
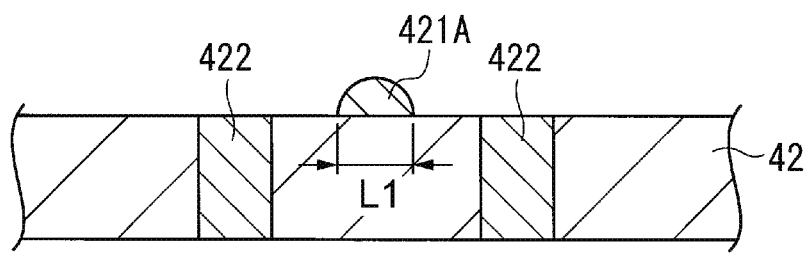
FIG. 19 is a sectional view schematically illustrating an example of a manufacturing process of the ultrasonic device according to the first embodiment.
Figure 20:
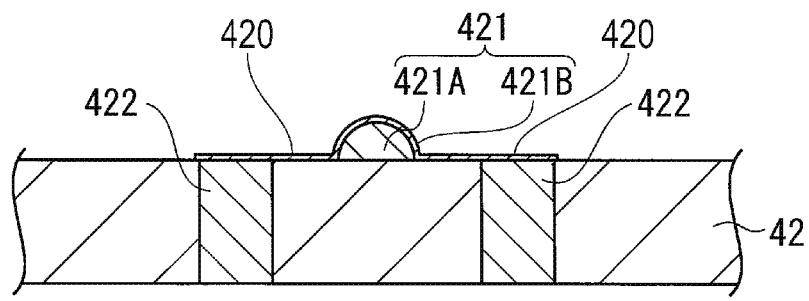
FIG. 20 is a sectional view schematically illustrating an example of a manufacturing process of the ultrasonic device according to the first embodiment.

Next, the conductor 421 is formed on the inner surface 42A side of the sealing plate 42 (step S22: conductor forming process (refer to FIG. 7)). As illustrated in FIG. 17, in step S22, first, a resin layer 53 for forming the resin core 421A is formed on the inner surface 42A of the sealing plate 42. Thereafter, as illustrated in FIG. 18, the resin layer 53 formed at positions other than the formation position of the resin core 421A is removed through etching. Next, as illustrated in FIG. 19, the resin layer 53 is heated and melted, and is then solidified, and thus substantially the hemispherical resin core 421A is formed. In the present embodiment, the resin core 421A is formed to have, for example, a width dimension (that is, the diameter $L_1$ of the surface on the inner surface 42A side) of 24 μm and a height dimension (height) of 12 μm. A shape of the resin core 421A may be adjusted by using a volume of the resin layer 53 before being melted, or the wettability of the inner surface 42A. As illustrated in FIG. 20, for example, a TiW layer (50 nm) and an Au layer (100 nm) are laminated in this order, and thus the through-hole connection line 420 and the conductive film 421B are formed.

Bonding Process

Figure 21:
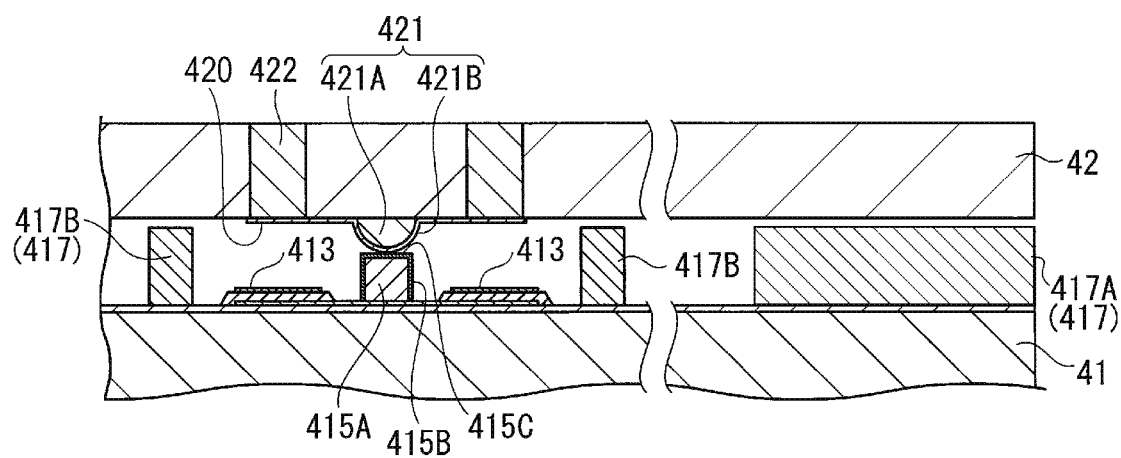
FIG. 21 is a sectional view schematically illustrating an example of a manufacturing process of the ultrasonic device according to the first embodiment.

Next, as illustrated in FIG. 7, a bonding process of bonding the element substrate 41 and the sealing plate 42 formed as described above together is performed (step S3). In step S3, as illustrated in FIG. 21, the sealing plate 42 is disposed on the element substrate 41. In this case, relative positions between the element substrate 41 and the sealing plate 42 are adjusted. In other words, positioning is performed so that the conductor 421 overlaps the corresponding wiring 415.

Figure 22:
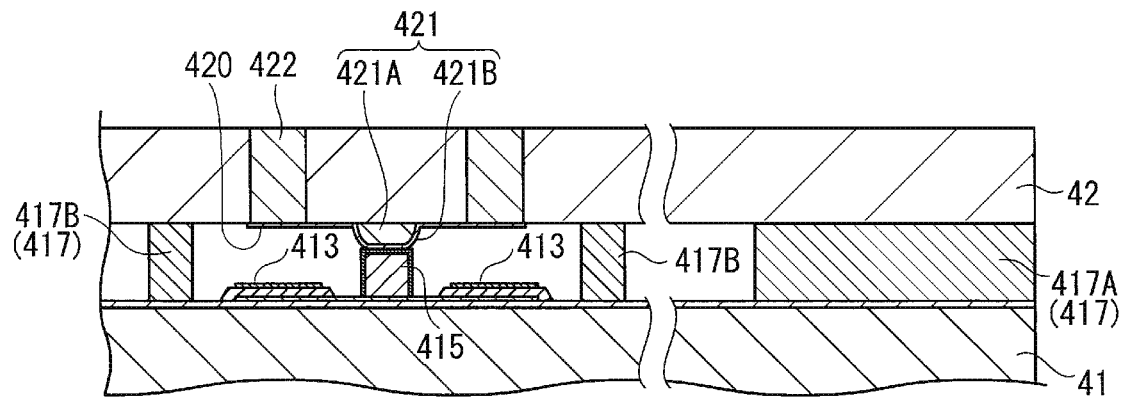
FIG. 22 is a sectional view schematically illustrating an example of a manufacturing process of the ultrasonic device according to the first embodiment.

As illustrated in FIG. 22, after the positioning is performed, at least one of the element substrate 41 and the sealing plate 42 is pressed in a direction in which the element substrate 41 and the sealing plate 42 come close to each other. Consequently, the conductor 421 is elastically deformed so as to come into close contact with the wiring 415. In this state, the element substrate 41 and the sealing plate 42 are heated (for example, for an hour at 200° C.). Consequently, the bond 417 is melted, and is then solidified again, and thus the element substrate 41 and the sealing plate 42 are bonded to each other.

Processing Process

Figure 23:
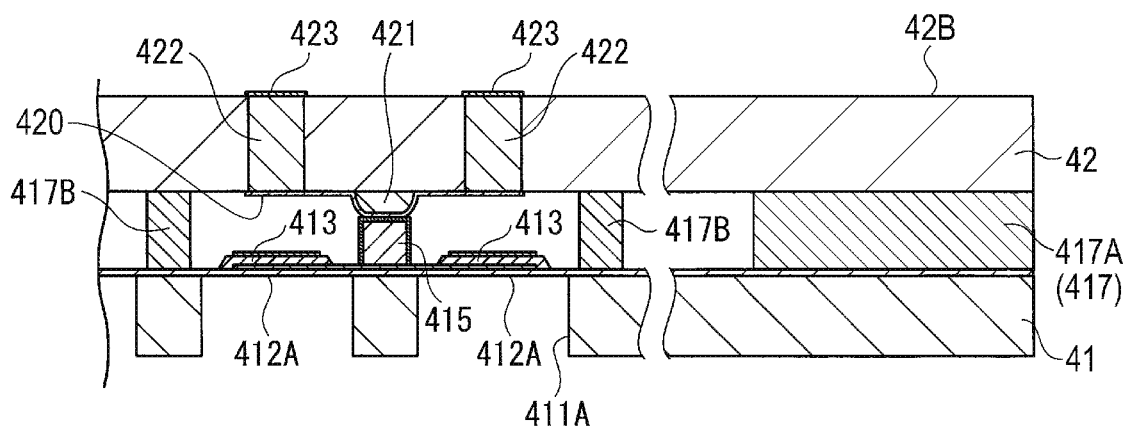
FIG. 23 is a sectional view schematically illustrating an example of a manufacturing process of the ultrasonic device according to the first embodiment.

Next, as illustrated in FIG. 7, a processing process of processing the element substrate 41 and the sealing plate 42 is performed (step S4). In step S4, as illustrated in FIG. 23, a thickness of the substrate main body 411 of the element substrate 41 is adjusted, and then the openings 411A are formed. A wiring including the lower electrode wires 423 is formed on the outer surface 42B of the sealing plate 42. A wiring on the outer surface 42B side of the sealing plate 42 may be formed in advance. Thereafter, as illustrated in FIG. 4, the openings 411A are filled with the acoustic matching layer 43, and then the protection film 44 is formed. In the above-described way, the ultrasonic device 22 is manufactured.

Advantageous Effects of First Embodiment

In the present embodiment, the distal end 415C of the wiring 415 is located further toward the sealing plate 42 side (closer to the sealing plate 42) than the distal end 413D of the piezoelectric element 413. In other words, the connection position between the conductor 421 and the wiring 415 is located further toward the sealing plate 42 side (extends further away from the substrate 41) than the distal end 413D of the piezoelectric element 413. In the present embodiment, the connection position is located further toward the sealing plate 42 side than the −Z side end part Rz of the vibration range of the ultrasonic transducer 45. In this configuration, even if a position difference occurs in the conductor 421, since a position of the conductor 421 is located further toward the sealing plate 42 side than the piezoelectric element 413, it is possible to suppress interference between the ultrasonic transducer 45 and the conductor 421.

Since interference between the ultrasonic transducer 45 and the conductor 421 due to a position difference can be suppressed, it is possible to appropriately perform wiring connection between the element substrate 41 and the sealing plate 42 even if alignment accuracy is lower than in a case where the wiring 415 is not formed.

It is possible to adjust a connection position between the wiring 415 and the conductor 421 according to a height dimension (height) of the wiring 415. Therefore, it is possible to easily adjust a connection position according to characteristics or the like of the ultrasonic transducer 45.

An aspect ratio of the wiring 415 is preferably 0.1 or more and 5 or less, and is about 1 in the present embodiment. Here, if the aspect ratio is equal to or less than 5, it is possible to prevent the wiring 415 from being inclined or bent due to pressing force from the conductor 421, and thus to improve the reliability of electrical connection. If the aspect ratio is equal to or more than 0.1, it is possible to prevent the wiring 415 from being deformed toward the +Z side due to pressing force from the conductor 421 and thus to prevent the conductor 421 from coming close to the ultrasonic transducer 45.

Here, the conductor 421 has the resin core 421A and the conductive film 421B covering the resin core 421A. The conductor 421 is in pressure contact with the wiring 415 so as to be elastically deformed. In this case, the conductor 421 is deformed along the distal end 415C, and is thus in close contact therewith. As mentioned above, since the resin core 421A is elastically deformed, the conductor 421 and the distal end 415C can be placed in close contact with each other, and thus it is possible to improve the reliability of electrical connection between the conductor 421 and the wiring 415.

The conductive film 421B is thinner than the resin core 421A, and thus does not hinder elastic deformation of the resin core 421A. Consequently, it is possible to further improve close contact between the conductor 421 and the distal end 415C. The stress applied to the element substrate 41 during pressure contact can be alleviated, and thus it is possible to prevent distortion or damage of the element substrate 41.

An area of the region in which the conductor 421 is bonded to the sealing plate 42 is larger than an area of the region in which the wiring 415 is connected to the conductor 421. The conductor 421 has the conductive film 421B which is curved toward the sealing plate 42 from the first connection region C1 to the outside along the XY plane. That is, the conductive film 421B is curved to be separated from the piezoelectric element 413 toward the piezoelectric element 413 side along the XY plane. Consequently, it is possible to suppress interference between the ultrasonic transducer 45 and the conductor 421.

The conductor 421 having the conductive film 421B can be easily formed by forming the resin core 421A by heating, melting, and then solidifying the resin layer 53, and by coating the resin core 421A with the conductive film 421B.

The resin core 421A is hemispherical during formation, and the end surface thereof on the inner surface 42A is substantially circular. As the diameter $L_1$ of the end surface, the distance d1 from the sealing plate 42 to the −Z side end part Rz of the vibration range of the ultrasonic transducer 45 satisfies the above Expression (1). Consequently, the conductor 421 can be disposed outside the vibration range of the ultrasonic transducer 45, and thus it is possible to further suppress interference between the ultrasonic transducer 45 and the conductor 421. Therefore, it is possible to appropriately drive the ultrasonic transducer 45.

In the present embodiment, the second bond 417B bonds the element substrate 41 to the sealing plate 42 in the array region Ar1. In this configuration, for example, the uniformity of a distance between the element substrate 41 and the sealing plate 42 can be improved compared with a configuration in which the element substrate 41 and the sealing plate 42 are bonded to each other by using only the first bond 417A. Consequently, for example, it is possible to prevent the occurrence of defective connection between the conductor 421 and the wiring 415 due to warping or the like of the element substrate 41 in the central part of the array region Ar1. Therefore, it is possible to improve the reliability of wiring connection between the element substrate 41 and the sealing plate 42.

The ultrasonic transducers 45 are provided on the rear surface 41A of the element substrate 41, and the ultrasonic transducers 45 include the first ultrasonic transducer 45B and the second ultrasonic transducer 45C. The wiring 415 is connected to the first ultrasonic transducer 45B and the second ultrasonic transducer 45C. The wiring 415 is provided between the first ultrasonic transducer 45B and the second ultrasonic transducer 45C in a plan view from the first direction 39A. In other words, a single wiring 415 is connected to the first ultrasonic transducer 45B and the second ultrasonic transducer 45C. Therefore, an area of the wiring 415 can be reduced compared with a case where the wiring 415 for the first ultrasonic transducer 45B only and the wiring 415 for the second ultrasonic transducer 45C only are provided. As a result, the first ultrasonic transducer 45B, the second ultrasonic transducer 45C, and the wiring 415 can be disposed on the element substrate 41 with higher density.

Second Embodiment

Hereinafter, a second embodiment will be described.

In the first embodiment, the conductor 421 has a substantially hemispherical conduction part with the wiring 415, and is provided to overlap (align with) the wiring 415 in a plan view in the Z direction. In contrast, the second embodiment is mainly different from the first embodiment in that a wiring and a conductor are provided to intersect each other in a plan view in the Z direction.

In the following description, the same constituent elements as those in the first embodiment are given the same reference numerals, and description thereof will be omitted or will be made briefly.

Configuration of Ultrasonic Device

Figure 24:
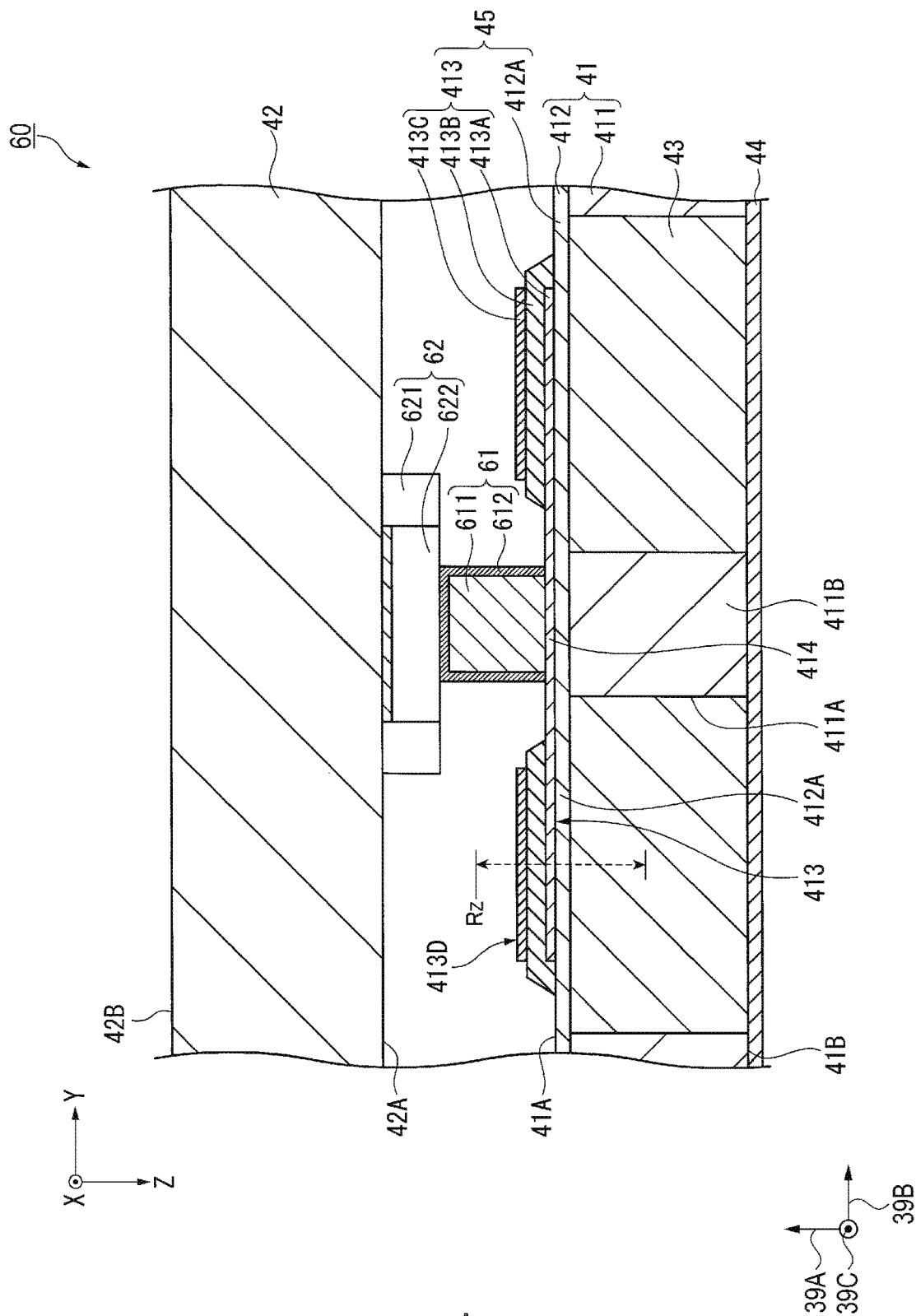
FIG. 24 is a sectional view illustrating a schematic configuration of main portions of an ultrasonic device according to a second embodiment.
Figure 25:
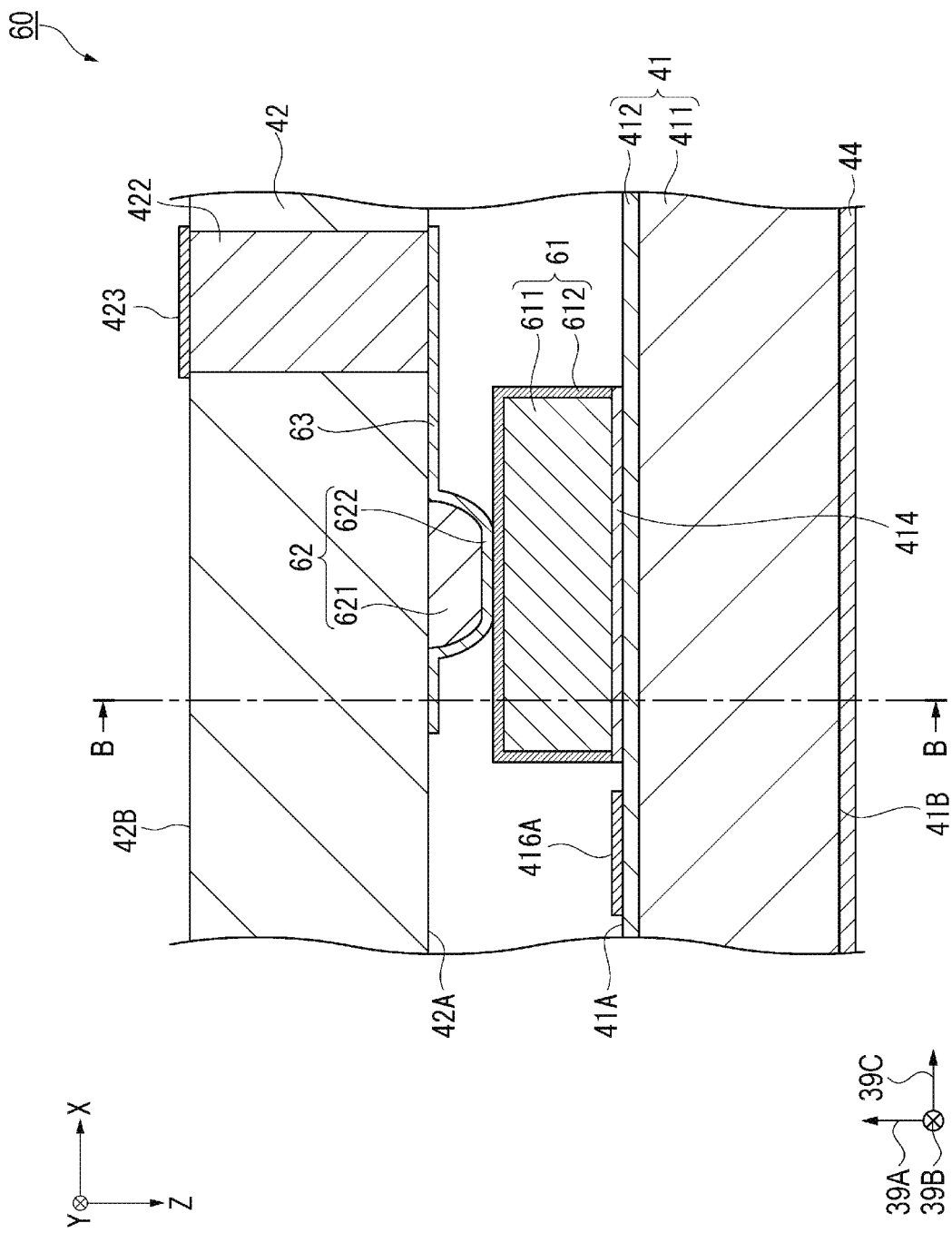
FIG. 25 is a sectional view illustrating a schematic configuration of main portions of the ultrasonic device according to the second embodiment.
Figure 26:
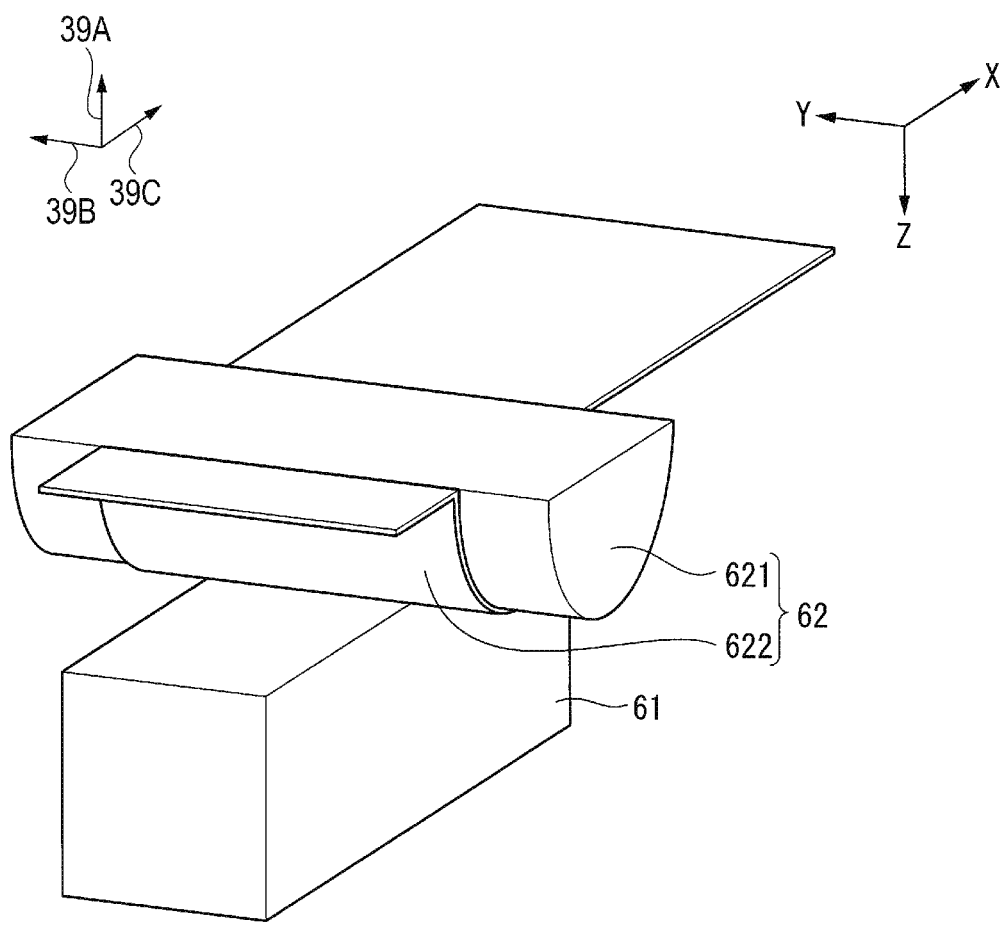
FIG. 26 is a perspective view illustrating a schematic configuration of main portions of the ultrasonic device according to the second embodiment.

FIG. 24 is a sectional view illustrating a schematic configuration of main portions of an ultrasonic device according to the second embodiment. FIG. 25 is a sectional view illustrating a schematic configuration of main portions of the ultrasonic device according to the second embodiment in FIG. 24. FIG. 26 is a perspective view illustrating a wiring and a conductor of the ultrasonic device according to the second embodiment. FIG. 24 is a sectional view of an ultrasonic device 60 taken along the line B-B in FIG. 25.

As illustrated in FIGS. 24 and 25, a wiring 61 is provided on the element substrate 41 in the ultrasonic device 60 of the second embodiment. A conductor 62 is provided on the sealing plate 42. The wiring 61 and the conductor 62 are in contact with and electrically connected to each other. Consequently, the lower electrode 413A of the piezoelectric element 413 of the ultrasonic transducer 45 is electrically connected to the circuit substrate 23 via the wiring 61, the conductor 62, the through-electrode 422, the lower electrode wire 423, and the like.

As illustrated in FIG. 25, in the second embodiment, a configuration in which a single through-electrode 422 is provided for a single conductor 62 is exemplified, but the number or an arrangement position of the through-electrode 422 is not limited to the configuration in the second embodiment.

Configuration of Wiring

The wiring 61 includes a main body 611 and a coating 612 and has electrical conductivity. The wiring 61 is configured in substantially the same manner as the wiring 415 of the first embodiment except that the wiring 61 is longitudinally extended in the X direction. The X direction in which the wiring 61 is longitudinally extended is referred to as a third direction 39C.

The coating 612 which is formed by using a conductive metal material is configured in substantially the same manner as the coating 415B of the first embodiment, and is formed to cover a surface of the main body 611.

The main body 611 is provided at a position overlapping the wall 411B such that the main body 611 is longitudinally extended in the X direction. In the main body 611, for example, a dimension thereof in the X direction is substantially the same as that of the opening 411A, and a dimension thereof in the Y direction is slightly smaller than that of the wall 411B. More specifically, the main body 611 has, for example, a dimension of 30 μm in the X direction, and a dimension (width dimension) of 10 μm in the Y direction and a dimension (height dimension) of 10 μm in the Z direction.

The main body 611 is formed, for example, on the lower electrode connection line 414 according to an electroplating method by using a conductive metal material in the same manner as in the first embodiment. In other words, in the second embodiment, a dimension of the lower electrode connection line 414 in the X direction is substantially the same as that of the opening 411A.

Configuration of Conductor

The conductor 62 is longitudinally extended in the Y direction, and the conductor 62 is provided on the inner surface 42A of the sealing plate 42 so as to intersect the wiring 61 in a plan view in the Z direction which is the first direction 39A (refer to FIG. 26). The conductor 62 includes a resin core 621 as a resin part, and a conductive film 622 as a conductive part which covers at least a part of the resin core 621 and electrically connected to the through-electrode 422. The conductor 62 is in pressure and close contact with the wiring 61 provided on the element substrate 41, and is electrically connected to the wiring 61.

The resin core 621 is formed by using an elastic resin material in the same manner as in the first embodiment. In the second embodiment, the resin core 621 is longitudinally extended in the Y direction which is orthogonal to the third direction 39C, and is formed in a substantially semi-cylindrical shape in which a ZX section before being elastically deformed is substantially semi-circular. The longitudinally extended direction of the conductor 62 is referred to as a second direction 39B. The ZX section of the resin core 621 is not limited to being substantially semi-circular, and may be substantially trapezoidal (a state in which corners of a trapezoid are rounded).

The conductive film 622 is provided to stride over (straddle) the resin core 621 along the X direction by using the same conductive material as in the first embodiment. Specifically, the conductive film 622 is provided at a position overlapping at least the wiring 61 on the resin core 621. On the resin core 621, a dimension of the conductive film 622 in the second direction 39B is larger than a dimension of the wiring 61 in the second direction 39B. A through-hole connection line 63 connected to the conductive film 622 is provided on the +X side of the conductive film 622. The through-hole connection line 63 extends to a position overlapping an end part of the through-electrode 422 on the +Z side. The conductive film 622 is electrically connected to the through-electrode 422 via the through-hole connection line 63.

The conductor 62 configured such that the resin core 621 is covered with the conductive film 622 is in pressure contact with the end part of the wiring 61 on the −Z side. In this case, the conductor 62 is in close contact with the wiring 61 by elastic force. As mentioned above, the wiring 61 and the conductor 62 can be placed in close contact with each other by the elastic force of the conductor 62, and thus it is possible to improve the connection reliability between the wiring 61 and the conductor 62. As illustrated in FIG. 24, the end part (crown) of the conductor 62 on the +Z side is located further toward the sealing plate 42 side than the −Z side end part Rz of the vibration range of the ultrasonic transducer 45. Thus, interference between the conductor 62 and the ultrasonic transducer 45 is suppressed. In the same manner as in the first embodiment, the conductive film 622 is much thinner than the resin core 621. Consequently, the conductive film 622 can be deformed according to elastic deformation of the resin core 621.

Advantageous Effects of Second Embodiment

The wiring 61 and the conductor 62 intersect each other in a plan view in the Z direction. Consequently, in the ultrasonic device 60, a position difference between the element substrate 41 and the sealing plate 42 is allowable during wiring connection, and thus it is possible to prevent the occurrence of defective connection. In other words, in the plan view, in a case where the wiring 61 and the conductor 62 do not intersect each other (for example, a case where the wiring 61 and the conductor 62 are parallel to each other or a connection surface between the wiring 61 and the conductor 62 is substantially rectangular or substantially circular), an area of a connection portion may be reduced due to a position difference between the element substrate 41 and the sealing plate 42, so that contact resistance increases. Appropriate electrical connection may not be performed due to a position difference. In contrast, since the wiring 61 and the conductor 62 are disposed to intersect each other, an allowable amount for a position difference in the X direction and the Y direction during alignment can be increased (refer to FIG. 26). Thus, alignment between the element substrate 41 and the sealing plate 42 can be easily performed, and wiring connection can also be easily performed. It is possible to improve connection reliability.

The wiring 61 is longitudinally extended in the X direction (third direction 39C), and the conductor 62 is longitudinally extended in the Y direction (second direction 39B). In the second direction 39B, a dimension of the conductive film 622 of the conductor 62 is larger than a dimension of the wiring 61. Consequently, even if a position difference between the element substrate 41 and the sealing plate 42 occurs in the second direction 39B during wiring connection, it is possible to maintain connection reliability on the basis of elastic force while allowing the position difference.

Modification Examples

The invention is not limited to the above-described embodiments, and configurations obtained through modifications, alterations, and combinations of the respective embodiments as desired within the scope capable of achieving the object of the invention are included in the invention.

For example, in the first embodiment, as an example, a description has been made of a configuration in which wiring connection between the element substrate 41 and the sealing plate 42 is performed by using the wiring 415 provided on the element substrate 41 and the conductor 421 provided on the sealing plate 42. However, the invention is not limited to the configuration of each embodiment, and may employ a configuration in each modification example which will be described later. A modification example of the first embodiment will be exemplified as each modification example which will be described later, but the same modification may be applied to the second embodiment.

First Modification Example

Figure 27:
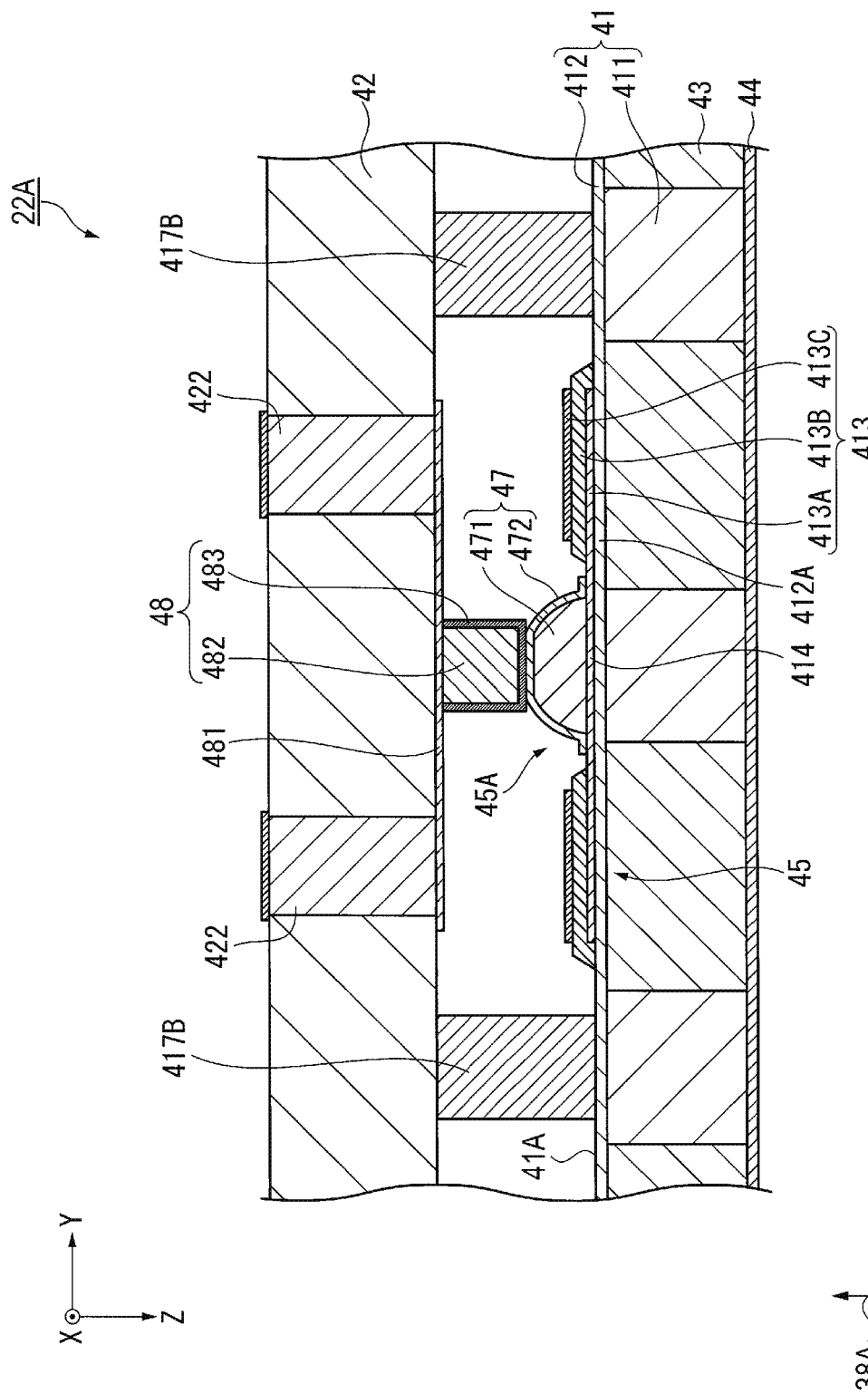
FIG. 27 is a sectional view illustrating a schematic configuration of an ultrasonic device according to a first modification example.

FIG. 27 is a sectional view illustrating a schematic configuration of an ultrasonic device 22A according to a first modification example.

As illustrated in FIG. 27, in the first modification example, a wiring 47 which is configured in the same manner as the conductor 421 of the first embodiment is provided on the element substrate 41. A conductor 48 which is configured in the same manner as the wiring 415 of the first embodiment is provided on the sealing plate 42. The wiring 47 and the conductor 48 are in contact with and electrically connected to each other.

The wiring 47 includes a resin core 471, and a conductive film 472 as a conductive part which covers the resin core 471. The resin core 471 is configured in the same manner as the resin core 421A, and is formed on the rear surface 41A of the element substrate 41. The conductive film 472 is configured in the same manner as the conductive film 421B, and is electrically connected to the lower electrode 413A of each ultrasonic transducer 45 forming the ultrasonic transducer group 45A.

The conductor 48 includes a main body 482 provided on a connection line 481, and a coating 483 coating the main body 482. The coating 483 is connected to the connection line 481 extracted from the through-electrode 422. The connection line 481 which is configured in the same manner as the lower electrode connection line 414 connects the through-electrode 422 to the conductor 48, and is a base layer of the main body 482 in the present modification example. The main body 482 and the coating 483 are respectively configured in the same manner as the main body 415A and the coating 415B.

Also in the first modification example, a height dimension (height) of the wiring 47 is larger than a height dimension (height) of the piezoelectric element 413. Consequently, it is possible to suppress interference between the conductor 48 and the ultrasonic transducer 45 and thus to easily perform wiring connection in the same manner as in the first embodiment. An end part (crown) of the wiring 47 on the −Z side is preferably located further toward the sealing plate 42 side than the −Z side end of the drive range of the ultrasonic transducer 45.

Since the wiring 47 is elastically deformed, close contact with the conductor 48 can be improved, and the stress applied to the element substrate 41 and the sealing plate 42 during connection can be alleviated.

In the first modification example, the wiring 47 includes the resin core 471, and the conductive film 472 which covers the resin core 471. In this configuration, when the conductor 48 is brought into contact with the wiring 47, the resin core 471 can be elastically deformed, and one of the wiring 47 and the conductor 48 can be deformed along the other thereof. Therefore, it is possible to improve close contact between the conductor 48 and the wiring 47, and thus to improve connection reliability.

The same modification as in the first modification example may be applied to the second embodiment. The wiring 47 is elongated in the X direction, and the conductor 48 is formed elongated in the Y direction. The wiring 47 and the conductor 48 may have shapes intersecting each other in a plan view viewed from the first direction 39A. Also in this case, a position difference between the element substrate 41 and the sealing plate 42 is allowable in a plane intersecting the first direction 39A during wiring connection, and thus it is possible to prevent the occurrence of defective connection between the wiring 47 and the conductor 48.

The wiring 47 includes the resin core 471 and the conductive film 472 covering at least a part of the resin core 471. Also in this case, when the conductor 48 is brought into contact with the wiring 47, the resin core 471 can be elastically deformed. The wiring 47 can be deformed along the conductor 48.

The X direction in which the wiring 47 is longitudinally extended is referred to as a second direction 38B. The Y direction in which the conductor 48 is longitudinally extended is referred to as a third direction 38C. The −Z direction is referred to as a first direction 38A. In the second direction 38B, a dimension of the conductive film 472 is larger than a dimension of the conductor 48. In this case, it is possible to maintain connection reliability on the basis of elastic force of the resin core 471 while allowing a position difference between the element substrate 41 and the sealing plate 42 in the second direction 38B during wiring connection.

Second Modification Example

Figure 28:
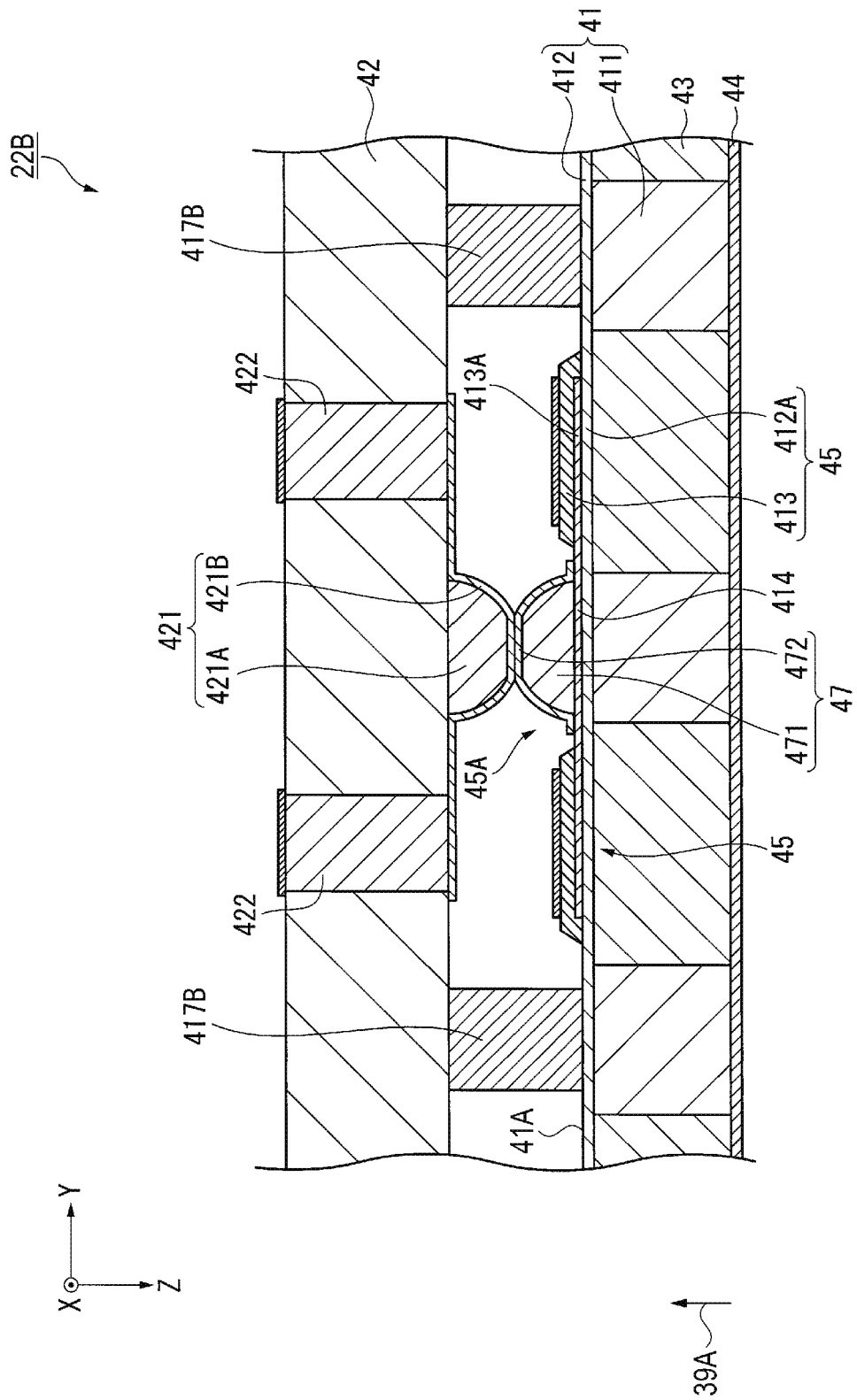
FIG. 28 is a sectional view illustrating a schematic configuration of an ultrasonic device according to a second modification example.

FIG. 28 is a sectional view illustrating a schematic configuration of an ultrasonic device 22B according to a second modification example.

As illustrated in FIG. 28, in the second modification example, the wiring 47 of the first modification example is provided on the element substrate 41, and the wiring 47 and the conductor 421 provided on the sealing plate 42 are in contact with and electrically connected to each other. In other words, the wiring 47 includes a resin core 471, and a conductive film 472 which covers the resin core 471. The conductor 421 includes a resin core 421A and a conductive film 421B which covers the resin core 421A.

In this configuration, when the conductor 421 and the wiring 47 are brought into contact with each other, the resin core 471 and the resin core 421A can be elastically deformed. Both of the wiring 47 and the conductor 421 can be deformed. Therefore, it is possible to improve close contact between the conductor 421 and the wiring 47, and thus to improve connection reliability.

Also in this configuration, it is possible to suppress interference between the conductor 421 and the ultrasonic transducer 45 and thus to easily perform wiring connection in the same manner as in the first embodiment. Since the wiring 47 and the conductor 421 are elastically deformed, close contact between the wiring 47 and the conductor 421 can be improved, and the stress applied to the element substrate 41 and the sealing plate 42 during connection can be alleviated.

Since both of the wiring 47 and the conductor 421 are elastically deformed, it is possible to further improve close contact between the wiring 47 and the conductor 421.

The same modification as in the second modification example may be applied to the second embodiment. The wiring 47 is elongated in the X direction, and the conductor 421 is elongated in the Y direction. The wiring 47 and the conductor 421 may have shapes intersecting each other in a plan view viewed from the first direction 39A. Also in this case, a position difference between the element substrate 41 and the sealing plate 42 is allowable in a plane intersecting the first direction 39A during wiring connection, and thus it is possible to prevent the occurrence of defective connection between the wiring 47 and the conductor 421.

The wiring 47 includes the resin core 471 and the conductive film 472 covering at least a part of the resin core 471. The conductor 421 includes the resin core 421A and the conductive film 421B covering at least a part of the resin core 421A. Also in this case, when the conductor 421 is brought into contact with the wiring 47, the resin core 471 and the resin core 421A can be elastically deformed. The wiring 47 and the conductor 421 can be deformed.

Third Modification Example

Figure 29:
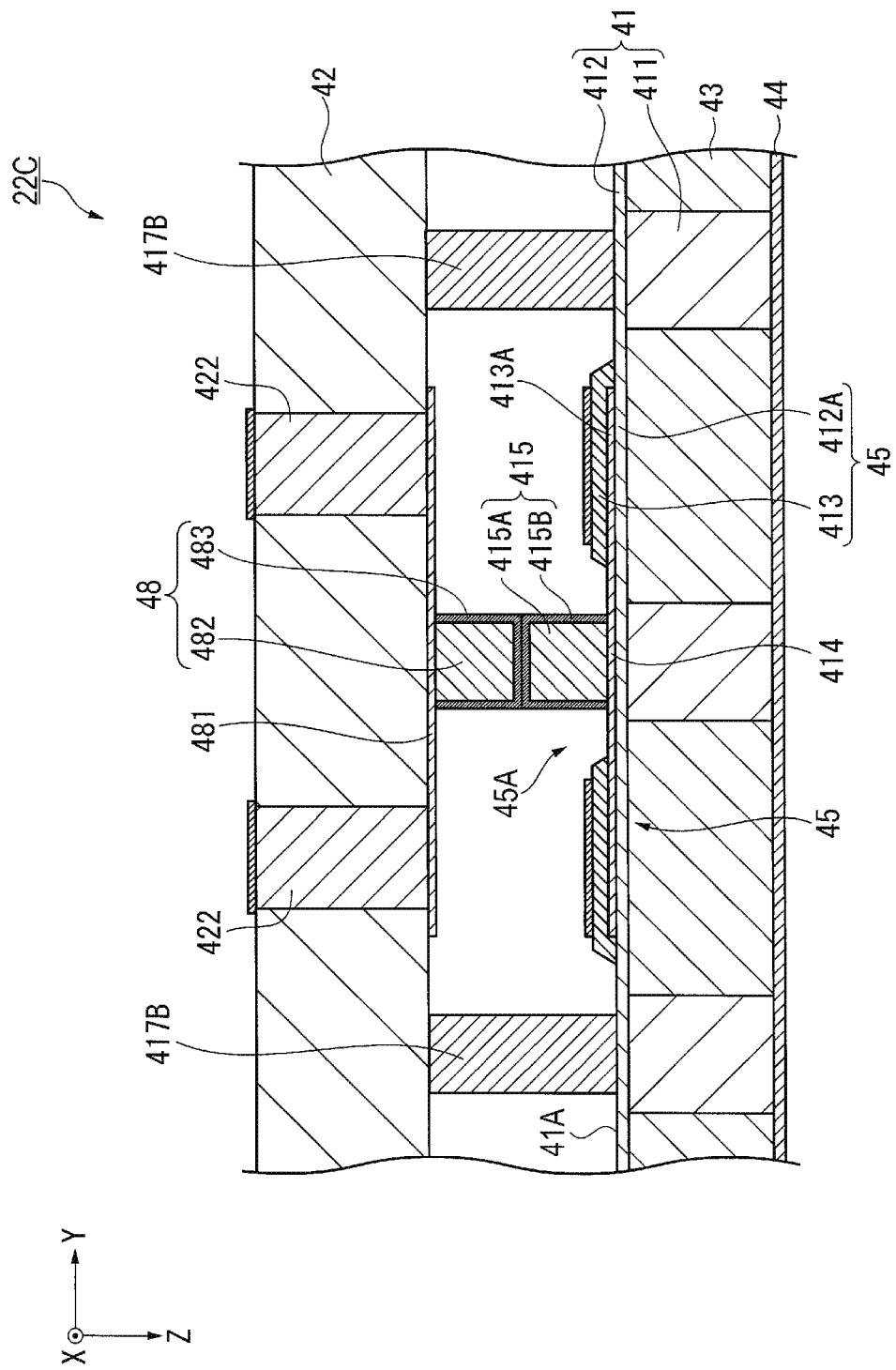
FIG. 29 is a sectional view illustrating a schematic configuration of an ultrasonic device according to a third modification example.

FIG. 29 is a sectional view illustrating a schematic configuration of an ultrasonic device 22C according to a third modification example.

As illustrated in FIG. 29, in the third modification example, the conductor 48 of the first modification example is provided on the sealing plate 42, and the conductor 48 and the wiring 415 provided on the element substrate 41 are in contact with and electrically connected to each other.

In this configuration, it is possible to suppress interference between the conductor 48 and the ultrasonic transducer 45 and thus to easily perform wiring connection in the same manner as in the first embodiment.

It is possible to adjust a distance between the element substrate 41 and the sealing plate 42 according to height dimensions (heights) of the wiring 415 and the conductor 48. Surfaces of the wiring 415 and the conductor 48 are bonded to each other through diffusion bonding as described above, so that the element substrate 41 and the sealing plate 42 can be bonded to each other at a plurality of positions in the array region Ar1, and thus it is possible to improve the in-plane uniformity of a distance between the element substrate 41 and the sealing plate 42.

Fourth Modification Example

Figure 30:
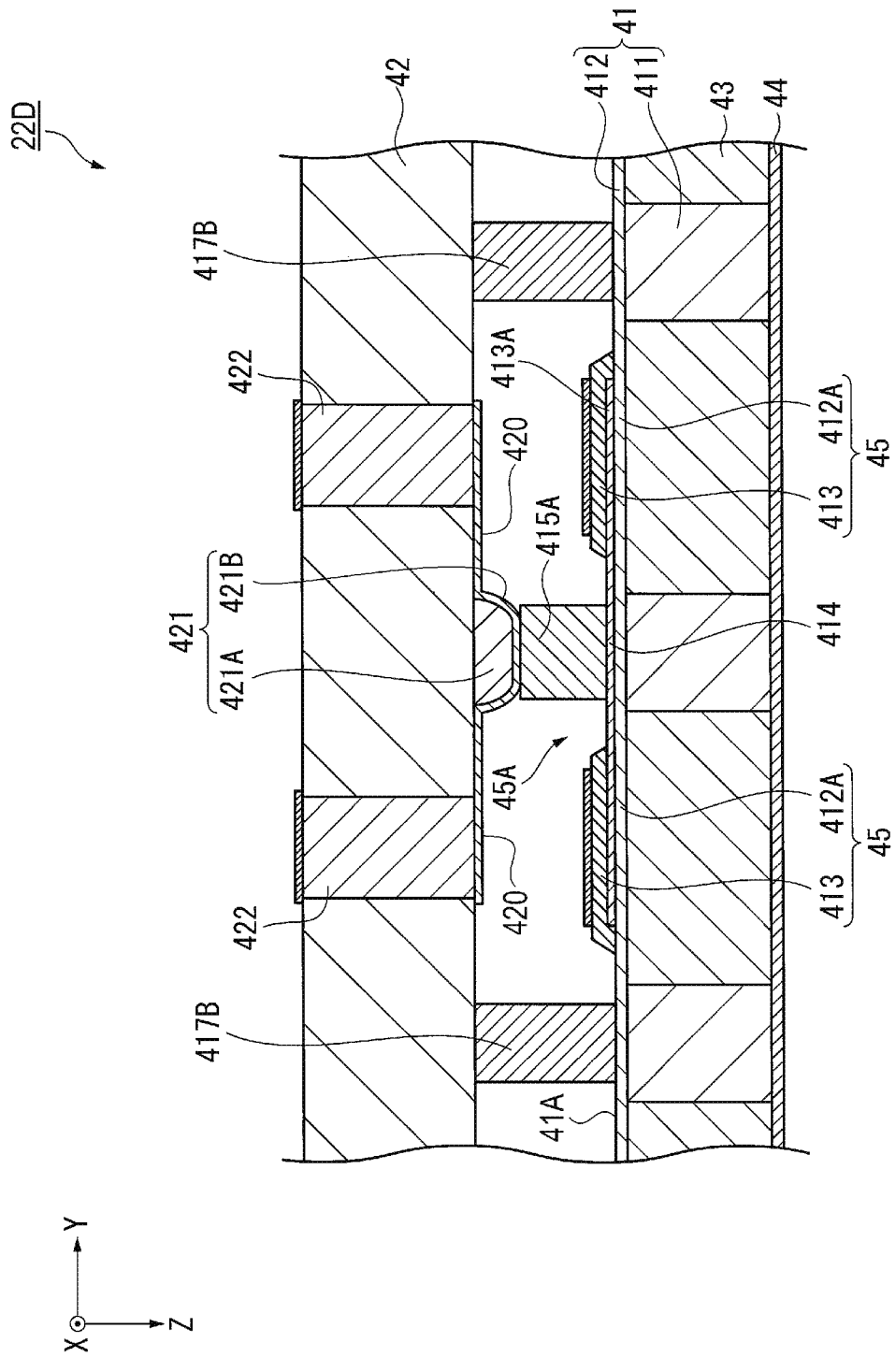
FIG. 30 is a sectional view illustrating a schematic configuration of an ultrasonic device according to a fourth modification example.

FIG. 30 is a sectional view illustrating a schematic configuration of an ultrasonic device 22D according to a fourth modification example.

As illustrated in FIG. 30, in the fourth modification example, the main body 415A of the first embodiment as a wiring is provided on the element substrate 41, and the main body 415A and the conductor 421 provided on the sealing plate 42 are in contact with and electrically connected to each other.

In this configuration, it is possible to suppress interference between the conductor 421 and the ultrasonic transducer 45 and thus to easily perform wiring connection in the same manner as in the first embodiment. The coating 415B is not formed, and thus a manufacturing process can be simplified.

Even in a case where bonding cannot be performed through diffusion bonding between the main body 415A and the conductor 421, the second bonds 417B are disposed with a bonding position interposed therebetween, and thus it is possible to improve the reliability of wiring connection.

Fifth Modification Example

Figure 31:
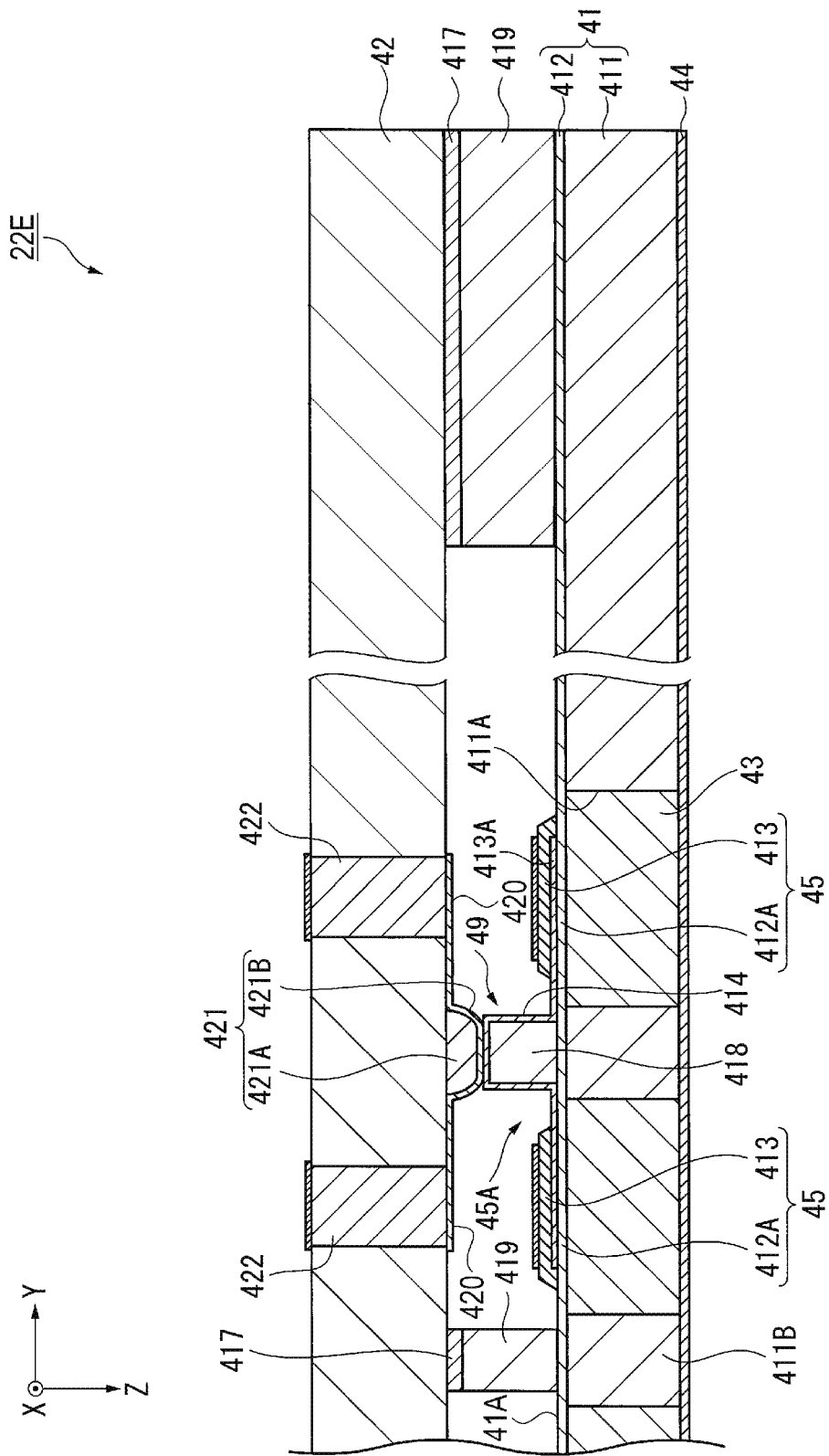
FIG. 31 is a sectional view illustrating a schematic configuration of an ultrasonic device according to a fifth modification example.
Figure 32:
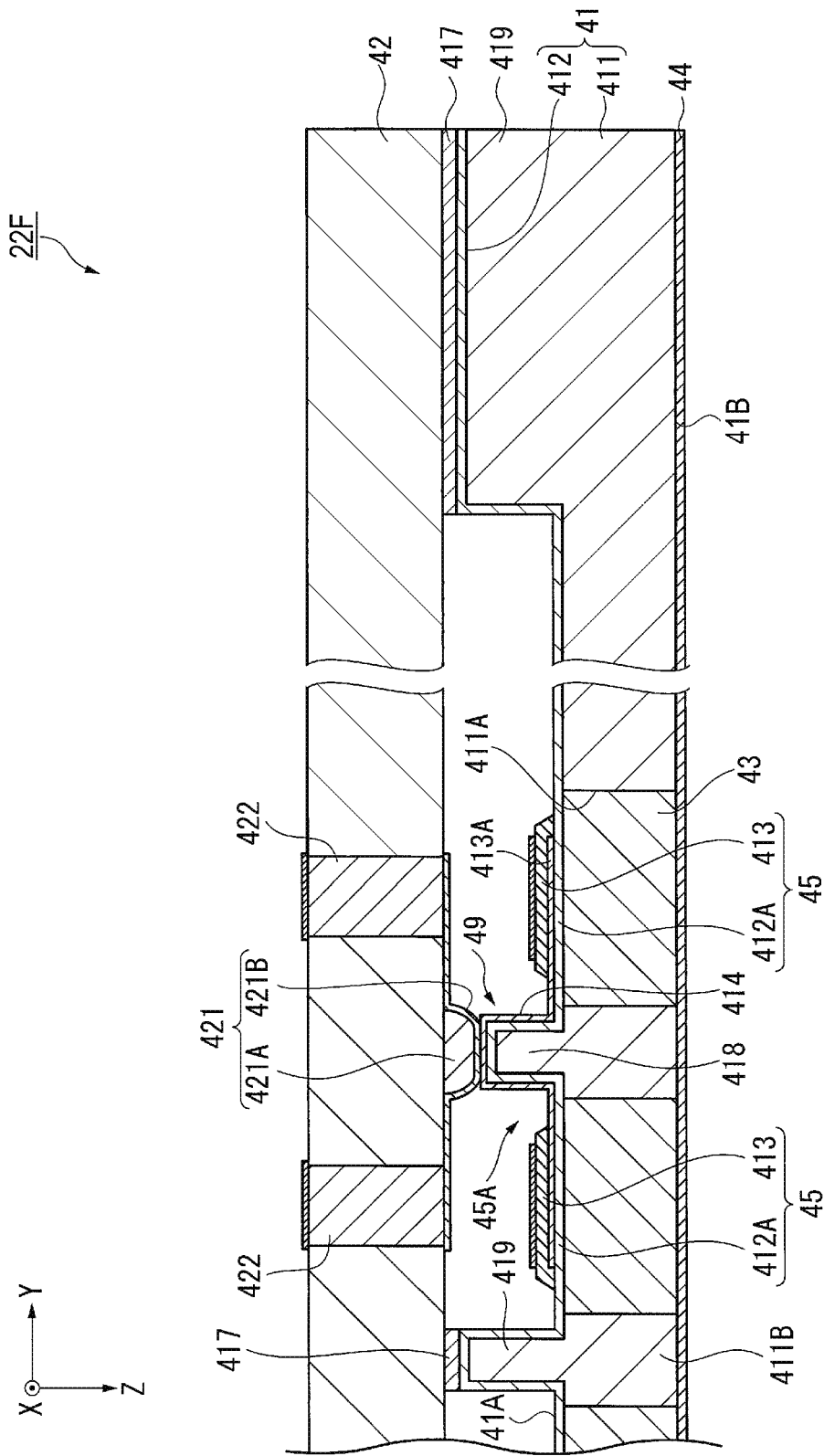
FIG. 32 is a sectional view illustrating a schematic configuration of the ultrasonic device according to the fifth modification example.

FIGS. 31 and 32 are sectional views illustrating schematic configurations of an ultrasonic device according to a fifth modification example.

As illustrated in FIG. 31, in an ultrasonic device 22E of the fifth modification example, the element substrate 41 is provided with a wiring 49 instead of the wiring 415 of the first embodiment, and the wiring 49 and the conductor 421 provided on the sealing plate 42 are in contact with and electrically connected to each other. Also in this configuration, it is possible to suppress interference between the conductor 421 and the ultrasonic transducer 45 and thus to easily perform wiring connection in the same manner as in the first embodiment.

A first protrusion 418 protruding toward the sealing plate 42 side is provided at a position facing the conductor 421 on the substrate main body 411. The lower electrode connection line 414 is provided to stride over the first protrusion 418. The wiring 49 is formed of the first protrusion 418 and apart of the lower electrode connection line 414. The first protrusion 418 is made of the same material as that of, for example, the substrate main body 411, and is bonded onto the vibration film 412. In the present modification example, the lower electrode connection line 414 may be formed by laminating a TiW layer (50 nm) and an Au layer (100 nm) in this order. As mentioned above, the Au layer is formed on the surface of the wiring 49, and thus the conductor 421 having an Au layer on the surface thereof and the wiring 49 can be bonded to each other through diffusion bonding.

A second protrusion 419 is provided at a formation position of the bond 417 on the substrate main body 411. The second protrusion 419 is formed in the same manner as the first protrusion 418, and protrudes toward the sealing plate 42 side. The bond 417 is formed on a surface of the second protrusion 419 on the sealing plate 42 side.

There may be a configuration in which the conductor 48 of the first modification example is provided instead of the conductor 421. The second protrusion 419 is formed, and thus a bonding height between the substrate main body 411 and the sealing plate 42 can be easily determined.

As illustrated in FIG. 32, in an ultrasonic device 22F, the first protrusion 418 and the second protrusion 419 may be formed by adjusting an etching amount, for example, when the rear surface 41A side of the substrate main body 411 is formed through etching. In this case, for example, the rear surface 41A side of the substrate main body 411 is etched such that the first protrusion 418 and the second protrusion 419 are formed, and then the vibration film 412 is formed. Next, the operation surface 41B side of the substrate main body 411 is etched, and thus the opening 411A is formed.

In the fifth modification example, the first protrusion 418 and the second protrusion 419 are formed by etching the substrate main body 411, but, for example, the second protrusion 419 may be formed on the sealing plate 42. The second protrusion 419 is formed according to the same method as that of the first protrusion 418, and protrudes toward the substrate main body 411 side. The bond 417 is formed on a surface of the second protrusion 419 on the substrate main body 411 side. The second protrusion 419 is formed, and thus the substrate main body 411 can be more easily formed than in a case where the first protrusion 418 and the second protrusion 419 are formed on the substrate main body 411. As described above, a bonding height between the substrate main body 411 and the sealing plate 42 can be easily determined.

Other Modification Examples

FIGS. 33 to 37 are sectional views illustrating schematic configurations of ultrasonic devices according to other modification examples.

In the above-described respective embodiments and modification examples, the second bonds 417B are disposed with each wiring interposed therebetween in one direction in the array region Ar1, but this is only an example.

Figure 33:
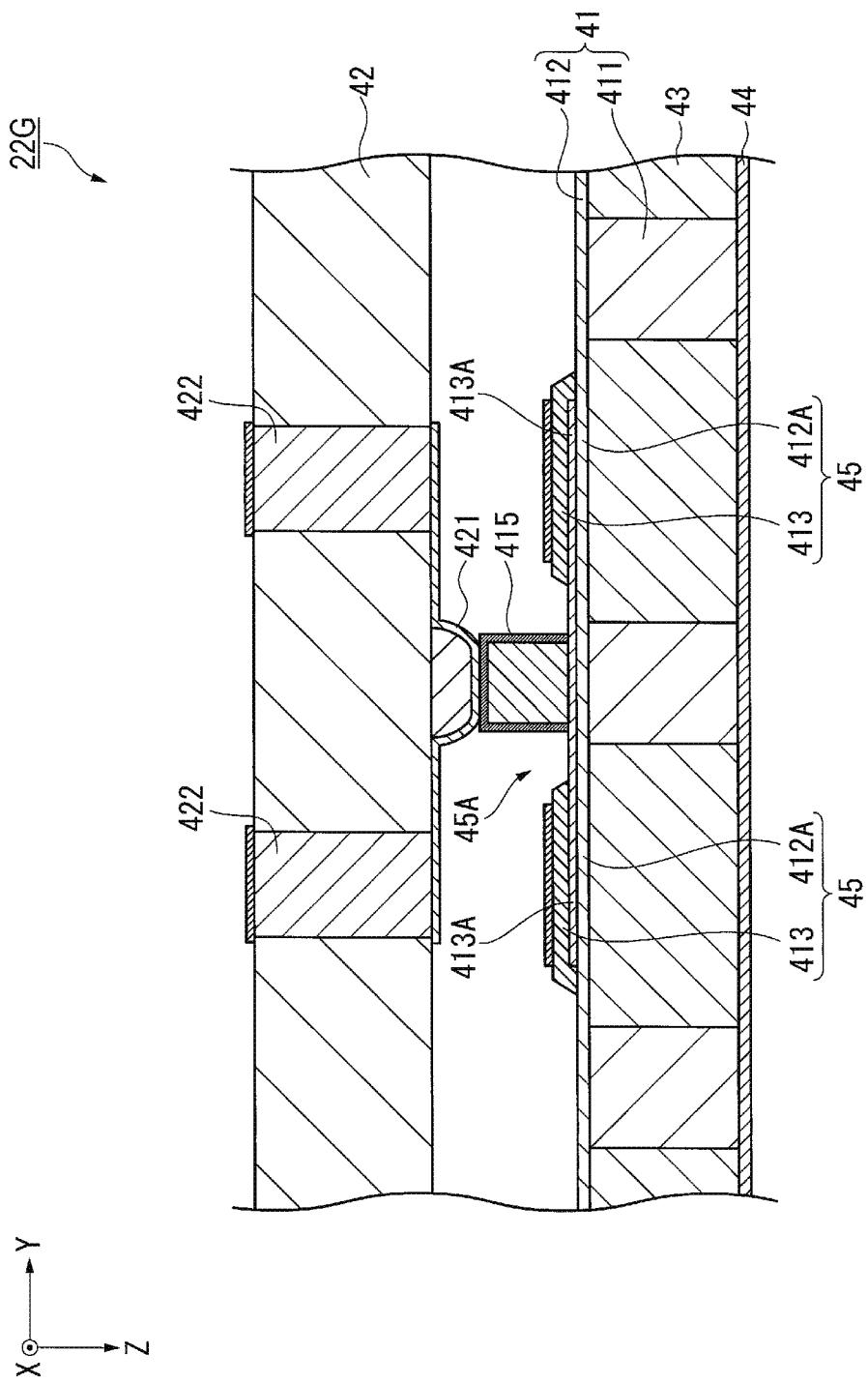
FIG. 33 is a sectional view illustrating a schematic configuration of an ultrasonic device according to another modification example.
Figure 34:
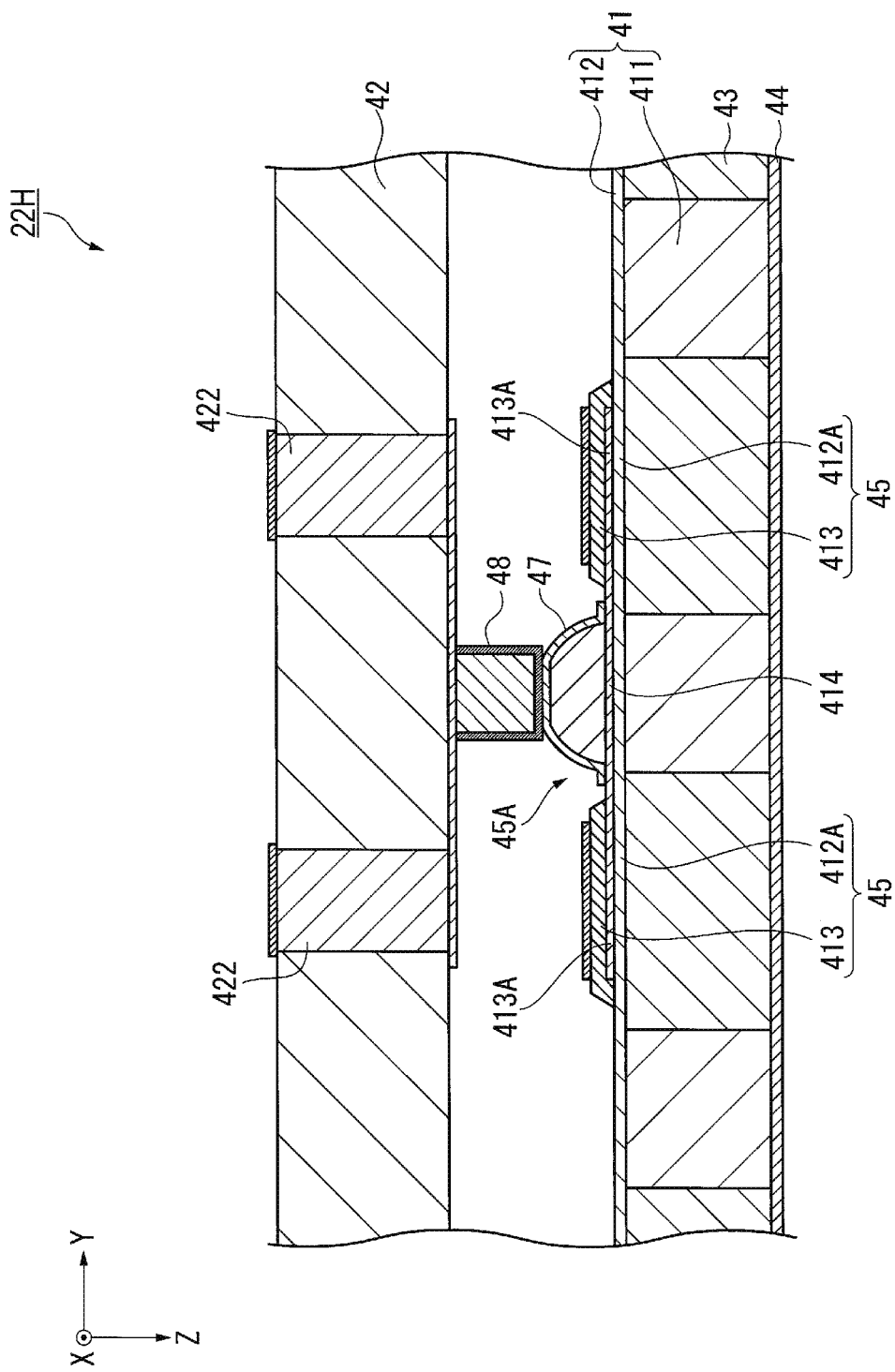
FIG. 34 is a sectional view illustrating a schematic configuration of an ultrasonic device according to still another modification example.
Figure 35:
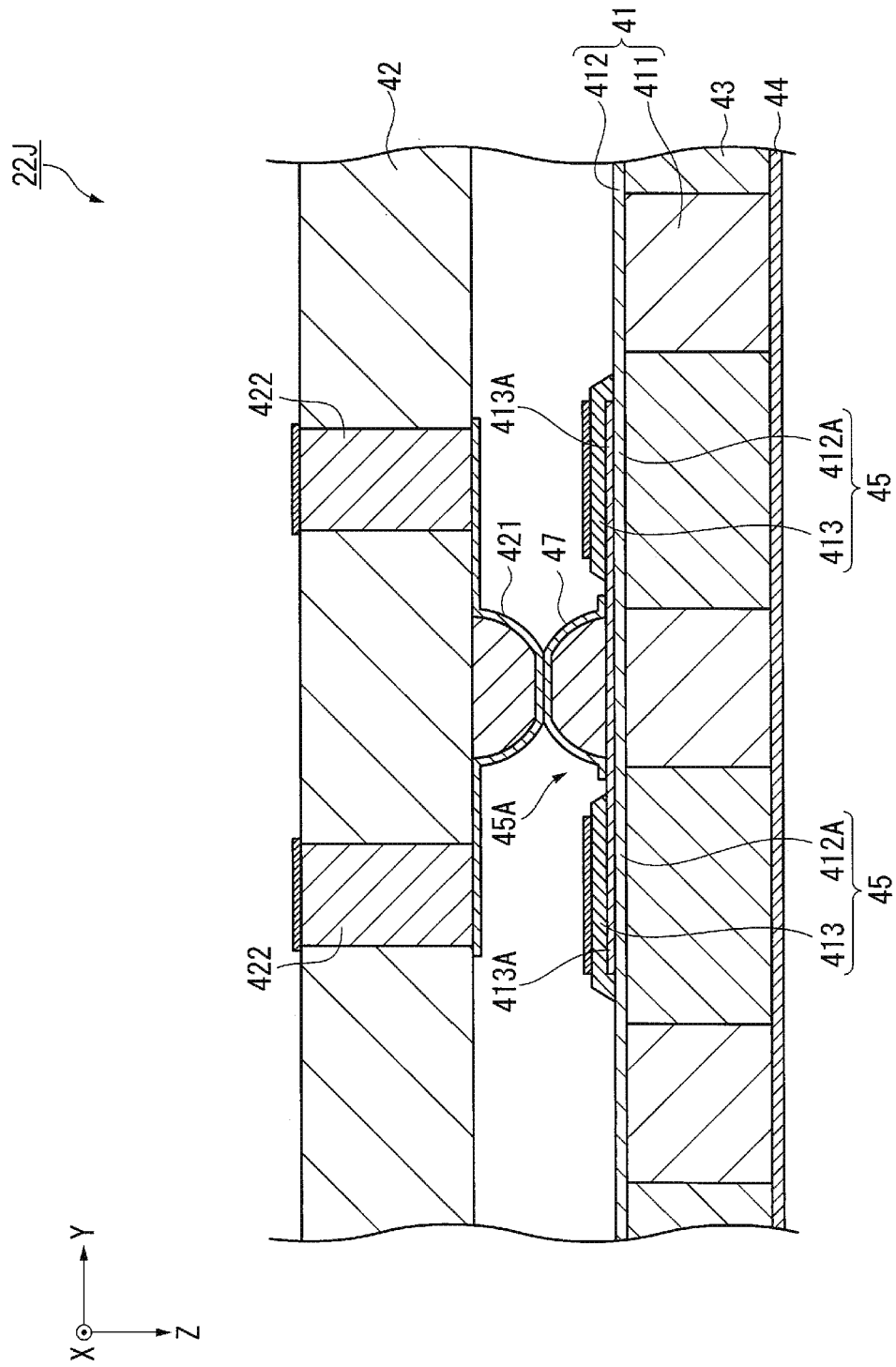
FIG. 35 is a sectional view illustrating a schematic configuration of an ultrasonic device according to still another modification example.
Figure 36:
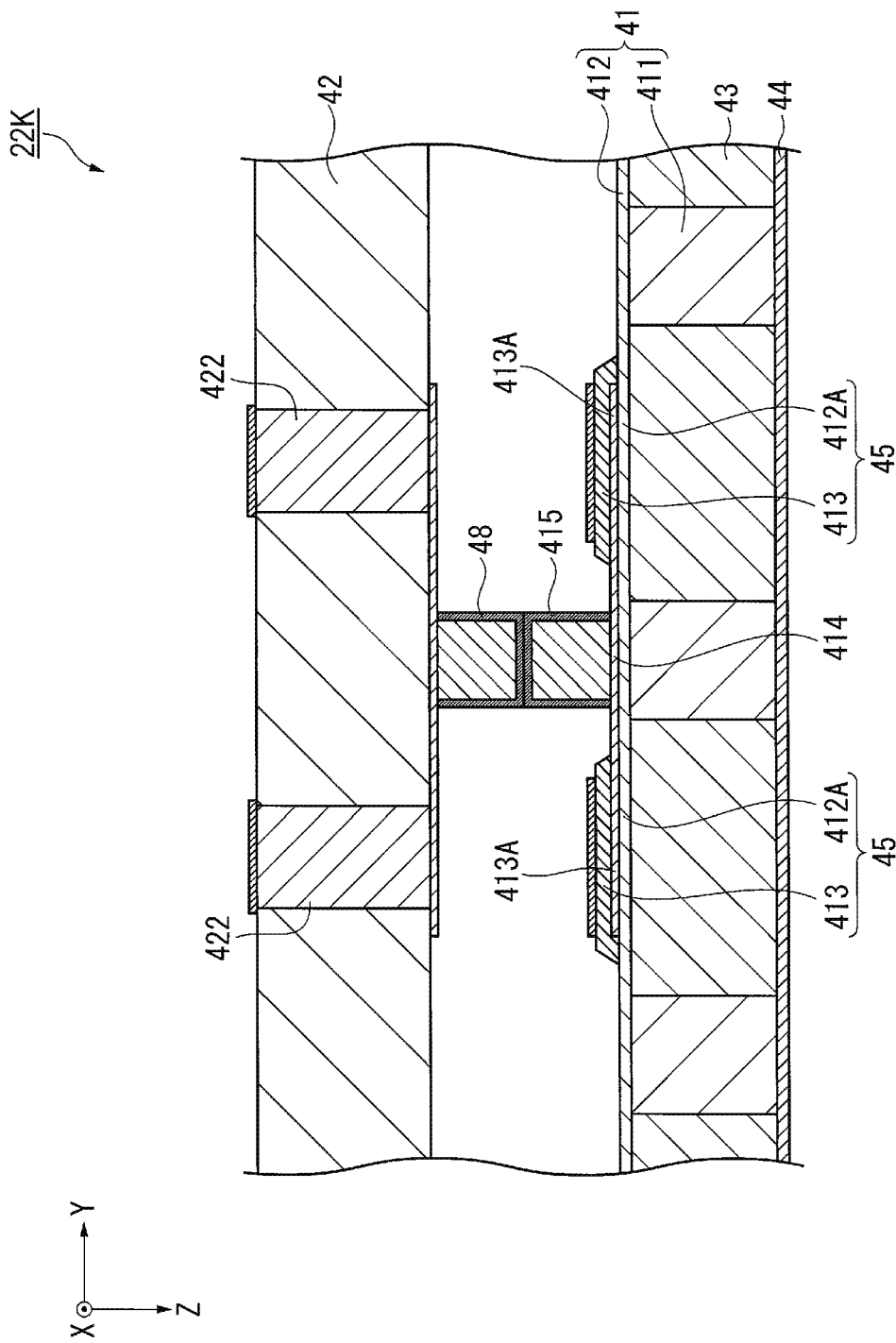
FIG. 36 is a sectional view illustrating a schematic configuration of an ultrasonic device according to still another modification example.
Figure 37:
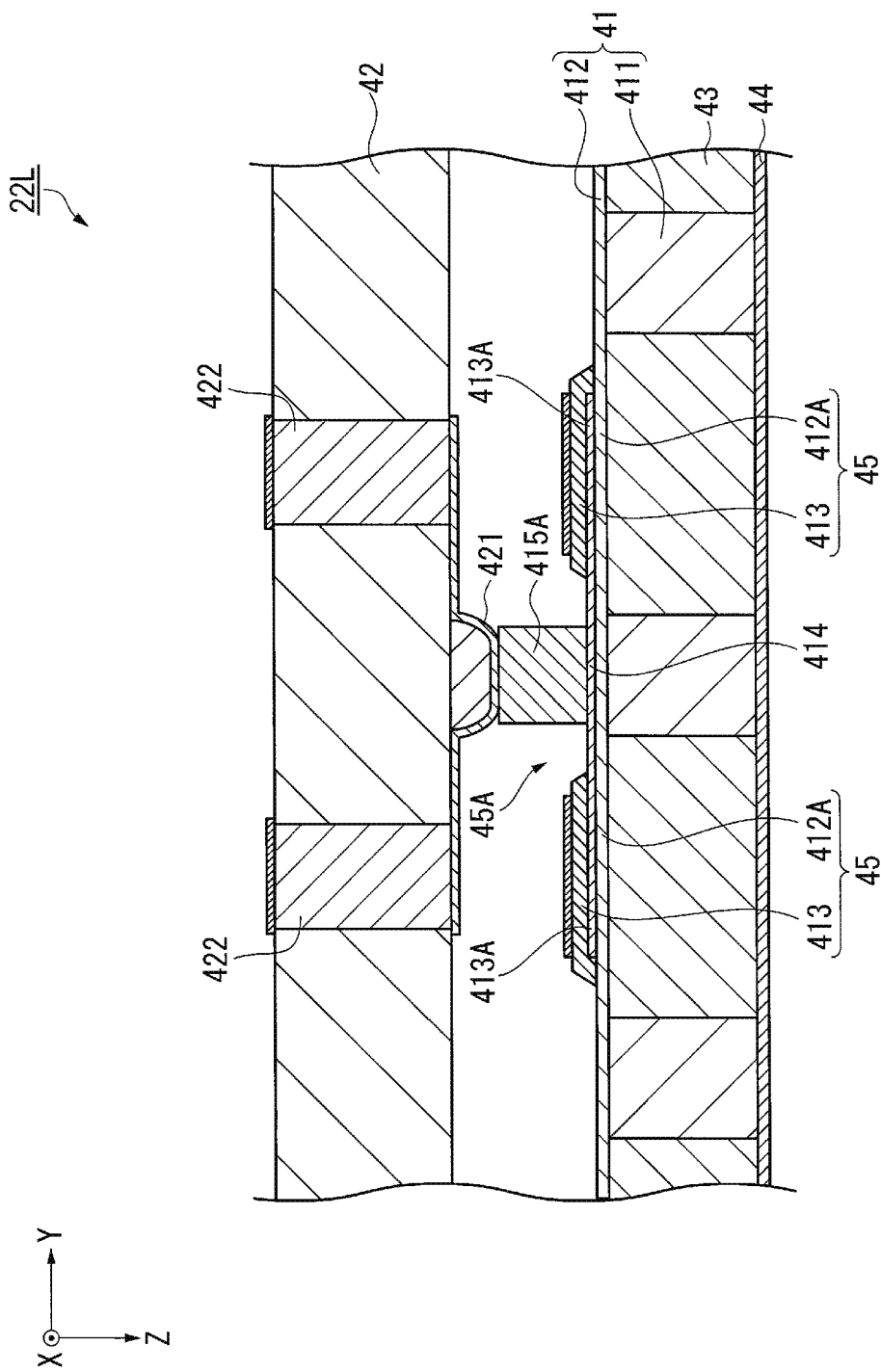
FIG. 37 is a sectional view illustrating a schematic configuration of an ultrasonic device according to still another modification example.

FIG. 33 illustrates a modification example of the first embodiment, and FIGS. 34 to 37 respectively illustrate modification examples of the first to fourth modification examples. As illustrated in FIGS. 33 to 37, for example, in an ultrasonic device 22G to an ultrasonic device 22L, the second bond 417B may not be provided in the array region Ar1. In this case, the element substrate 41 and the sealing plate 42 are bonded to each other via the first bond 417A. Even in this configuration, the element substrate 41 and the sealing plate 42 have the sufficient rigidity, and thus it is possible to secure the connection reliability between the wiring and the conductor. In a case where diffusion bonding between the wiring and the conductor is possible, it is possible to improve connection reliability, and also to simplify a configuration due to the second bond 417B not being provided.

A pair of the second bonds 417B may be disposed for some of the wirings disposed in the array region Ar1. Not only a configuration in which two second bonds 417B are disposed with the wiring interposed in one direction therebetween but also a configuration in which a single second bond 417B is disposed may be employed. For example, the second bond 417B may be disposed on the +Y side or the −Y side of each wiring.

In the above-described respective embodiments, the conductor has a configuration in which the resin core is coated with the conductive film thinner than the resin core, but any other configuration may be used. For example, there may be a configuration in which a conductive layer having substantially the same thickness as that of the resin core is laminated on the resin core, and the conductive layer may be thicker than the resin core. If the resin core is thicker than the conductive layer, it is possible to further alleviate the stress applied to the element substrate 41 or the sealing plate 42 due to elasticity of the conductor.

In the first embodiment, the conductor 421 includes the conductive film 421B, but is not limited thereto, and may include an inclined part which is inclined in a direction of becoming distant (extending away) from the piezoelectric element 413 toward the element substrate 41 from the sealing plate 42. This inclined part may have a planar or curved inclined surface, and may have an inclined surface including a planar surface and a curved surface.

In the above-described respective embodiments, the ultrasonic transducer group 45A formed of two ultrasonic transducers 45 is used as a single transmission/reception channel, but the ultrasonic transducer group 45A may be formed by connecting the lower electrodes 413A of three or more ultrasonic transducers 45 to each other. There may be a configuration in which the lower electrodes 413A of the respective ultrasonic transducers 45 are separate from each other, and thus each of the ultrasonic transducers 45 is individually driven. In this case, each ultrasonic transducer 45 may function as a single transmission/reception channel.

In the above-described respective embodiments, a description has been made of an example of the ultrasonic device 22 having a two-dimensional array structure in which the ultrasonic transducer groups 45A each functioning as a single transmission/reception channel are disposed in a matrix in the array region Ar1 of the element substrate 41, but this is only an example. For example, the ultrasonic device may have a one-dimensional array structure in which a plurality of transmission/reception channels are disposed along one direction. For example, the ultrasonic transducer group 45A may be formed of a plurality of ultrasonic transducers 45 disposed along the X direction, and a plurality of ultrasonic transducer groups 45A are disposed in the Y direction so as to form the ultrasonic array AL having a one-dimensional array structure.

In the above-described embodiments, a description has been made of an example of a configuration in which the ultrasonic transducer 45 is formed of the vibration film 412 and the piezoelectric element 413 formed on the vibration film 412, but this is only an example. For example, the ultrasonic transducer 45 may be configured to include a flexible film 412A, a first electrode provided on the flexible film 412A, and a second electrode provided at a position opposing the first electrode in a sealing plate. The first electrode and the second electrode form an electrostatic actuator as a vibrator. In this configuration, an ultrasonic wave can be transmitted by driving the electrostatic actuator, and an ultrasonic wave can be detected by detecting electrostatic capacitance between the electrodes.

In the above-described respective embodiments, an ultrasonic apparatus which measures an organ of a living body has been described as an example of an electronic apparatus, but the invention is not limited thereto. For example, the configurations of the above-described respective embodiments and modification examples may be applied to a measurement apparatus which measures various structural bodies, and detects a defect of a structural body or inspects aging thereof. This is also the same for a measurement apparatus which measures, for example, a semiconductor package or a wafer, and detects a defect of such a measurement target.

In the above-described embodiments, a description has been made of an example of a configuration in which the ultrasonic transducer is provided on the element substrate, but the invention is not limited thereto. For example, the configurations of the respective embodiments and modification examples may be applied to a mounting structure including a first substrate provided with an electronic component such as a semiconductor IC, that is, an functional element, and a second substrate electrically connected to the first substrate, or an image display device or an image forming device in which the mounting structure is provided in a case. In other words, a wiring which is provided on the first substrate and is connected to the electronic component and a conductor which is provided on the second substrate and is connected to the wiring are connected to each other further toward the second substrate side than the electronic component, and thus it is possible to suppress interference between the functional element and the conductor and thus to appropriately and easily perform wiring connection between the first substrate and the second substrate.

A specific structure, when the invention is implemented, may be configured as desired by combining the respective embodiments and modification examples within the scope of being capable of achieving the object of the invention, and may be changed to other structures as desired.

The entire disclosure of Japanese Patent Application No. JP 2017-092818 filed May 9, 2017 is expressly incorporated by reference herein.

What is claimed is:
1. A mounting structure comprising:
a first substrate that has a first surface;
a functional element on the first surface;
a wiring on the first surface at a position spaced apart from the functional element, the wiring being electrically connected to the functional element, the wiring upwardly projecting from the first surface of the first substrate;
a second substrate that has a second surface facing the first surface; and
a conductor on the second surface, the conductor being electrically connected to the wiring and the functional element, a part of the conductor downwardly projecting from the second surface toward the wiring,
wherein a shortest distance between the functional element and the second substrate is longer than a distance between a contact position and the second substrate, and the wiring is physically connected to the conductor at the contact position.

2. The mounting structure according to claim 1, wherein an area of a region in which the conductor is bonded to the second substrate is larger than an area of a region in which the wiring is physically connected to the conductor.

3. The mounting structure according to claim 1, wherein at least one of the wiring and the conductor includes a resin core and a conductive film over the resin core.

4. The mounting structure according to claim 3, wherein, in a first direction extending from the first substrate to the second substrate, a thickness of the resin core at a position overlapping a connection region between the conductor and the wiring is larger than a thickness of the conductive film.

5. The mounting structure according to claim 3, wherein the resin core has a substantially hemispherical shape protruding from the second surface while the conductor is not elastically deformed, and
a maximum diameter of an end surface of the resin core on the second substrate is L, a distance from the second substrate to the functional element is d, and d>L/2.

6. The mounting structure according to claim 1, wherein the wiring and the conductor intersect each other in a first direction extending from the first substrate to the second substrate.

7. The mounting structure according to claim 6, wherein at least one of the wiring and the conductor includes a resin core and a conductive film over at least a part of the resin core.

8. The mounting structure according to claim 7, wherein one of the wiring and the conductor longitudinally extends in a second direction which is parallel to the first surface,
wherein the other of the wiring and the conductor longitudinally extends in a third direction which is parallel to the first surface and intersects the second direction, and
wherein, a dimension of the conductive film in the second direction is larger than a dimension of the other of the wiring and the conductor in the second direction.

9. The mounting structure according to claim 1, wherein the wiring is made of a metal material, and
a ratio of a height of the wiring in a normal direction of the first surface to a width of the wiring on the first surface is 0.1 or more and 5 or less.

10. The mounting structure according to claim 1, wherein the functional element includes a first functional element and a second functional element, and
wherein the wiring is electrically connected to the first functional element and the second functional element, and the wiring is provided between the first functional element and the second functional element in a plan view.

11. The mounting structure according to claim 1, wherein the functional element includes a vibrator that vibrates in a first direction extending from the first substrate to the second substrate.

12. The mounting structure according to claim 11, wherein a connection position between the wiring and the conductor is located further toward the second substrate than a vibration range of the vibrator in the first direction.

13. The mounting structure according to claim 11, wherein the functional element is an ultrasonic transducer including a flexible film formed on the first substrate, and the vibrator provided on the flexible film.

14. The mounting structure according to claim 1, further comprising:
a bond that bonds the first substrate to the second substrate,
wherein the first substrate has a functional region in which a plurality of the functional elements are formed, and
wherein the bond bonds the first substrate to the second substrate in the functional region.

15. The mounting structure according to claim 1, wherein the functional element is a vibrator.

16. An ultrasonic probe comprising:
a first substrate that has a first surface;
a vibrator on the first surface;
a wiring on the first surface at a position spaced apart from the vibrator on the first surface, the wiring being electrically connected to the vibrator, the wiring upwardly projecting from the first surface of the first substrate;
a second substrate that has a second surface facing the first surface;
a conductor on the second surface, the conductor being electrically connected to the wiring and the vibrator, a part of the conductor downwardly projecting from the second surface toward the wiring; and
a case in which the first substrate, the wiring, the second substrate, and the conductor are housed,
wherein a shortest distance between the vibrator and the second substrate is longer than a distance between a contact position and the second substrate, and the wiring is physically connected to the conductor at the contact position.

17. An electronic apparatus comprising:
a first substrate that has a first surface;
a functional element on the first surface;
a wiring on the first surface at a position spaced apart from the functional element, the wiring being electrically connected to the functional element, the wiring upwardly projecting from the first surface of the first substrate;
a second substrate that has a second surface facing the first surface;
a conductor on the second surface, the conductor being electrically connected to the wiring and the functional element, a part of the conductor downwardly projecting from the second surface toward the wiring; and
a controller that controls the functional element,
wherein a shortest distance between the functional element and the second substrate is longer than a distance between a contact position and the second substrate, and the wiring is physically connected to the conductor at the contact position.

18. The electronic apparatus according to claim 17, wherein the functional element is a vibrator.

\* \* \* \* \*